US010143828B2

(12) United States Patent
Furnish et al.

(10) Patent No.: US 10,143,828 B2
(45) Date of Patent: Dec. 4, 2018

(54) MEDICAL VALVE WITH A VARIABLE DIAMETER SEAL

(71) Applicant: FREUDENBERG MEDICAL, LLC, Carpinteria, CA (US)

(72) Inventors: Greg Furnish, Louisville, KY (US); Anthony Appling, Crestwood, KY (US); Ben Morris, Jeffersonville, IN (US); Simon Furnish, Louisville, KY (US)

(73) Assignee: FREUDENBERG MEDICAL, LLC, Carpinteria, CA (US)

( * ) Notice: Subject to any disclaimer, the term of this patent is extended or adjusted under 35 U.S.C. 154(b) by 0 days.

(21) Appl. No.: 15/624,755

(22) Filed: Jun. 16, 2017

(65) Prior Publication Data

US 2017/0281920 A1 Oct. 5, 2017

Related U.S. Application Data

(63) Continuation-in-part of application No. 15/483,089, filed on Apr. 10, 2017, which is a continuation of
(Continued)

(51) Int. Cl.
*A61M 5/14* (2006.01)
*A61M 39/06* (2006.01)
(Continued)

(52) U.S. Cl.
CPC ..... *A61M 39/0613* (2013.01); *A61B 1/00137* (2013.01); *A61B 1/018* (2013.01);
(Continued)

(58) Field of Classification Search
CPC .. A61M 39/06; A61M 39/02; A61M 39/0631; A61B 1/018; A61B 1/00137
See application file for complete search history.

(56) References Cited

U.S. PATENT DOCUMENTS 5,484,418 A 1/1996 Quiachon et al.
5,634,908 A 6/1997 Loomas
(Continued)

FOREIGN PATENT DOCUMENTS

EP 0426407 A2 5/1991
JP 200316986 A 11/2000
WO 2005058409 A1 6/2005

OTHER PUBLICATIONS

Search Report dated Nov. 23, 2015 in corresponding European Patent Application No. 15175941.2.

*Primary Examiner* — Edelmira Bosques
(74) *Attorney, Agent, or Firm* — Dickinson Wright PLLC

(57) ABSTRACT

A medical valve assembly includes a tube extending between a first tube end and a second tube end to define a passageway extending along a longitudinal axis between the ends. A plunger plate extends radially from the second tube end of the tube, and a valve housing surrounds the tube about the second tube end and extends from a first valve housing end to a second valve housing end. The valve housing includes a housing flange extending radially inwardly from the second valve housing end and disposed in spaced relationship with the plunger plate to define a distance dimension D extending therebetween. An elastomeric seal is compressed between the plunger plate and the housing flange, and one of the valve housing and the tube is axially movable relative to the other to vary the distance between said plunger plate and said housing flange and adjust an inner diameter of the elastomeric seal.

14 Claims, 20 Drawing Sheets

Related U.S. Application Data application No. 14/326,593, filed on Jul. 9, 2014, now Pat. No. 9,616,213.

(51) Int. Cl.
*A61B 1/00* (2006.01)
*A61B 1/018* (2006.01)

(52) U.S. Cl.
CPC ....... *A61M 39/06* (2013.01); *A61M 2039/062* (2013.01); *A61M 2039/0633* (2013.01); *A61M 2039/0673* (2013.01)

(56) References Cited

U.S. PATENT DOCUMENTS

| | | |
|---|---|---|
| 6,458,103 B1 | 10/2002 | Albert et al. |
| 6,572,590 B1 | 6/2003 | Stevens et al. |
| 7,967,790 B2 | 6/2011 | Whiting et al. |
| 8,025,641 B2 | 9/2011 | Bettuchi |
| 2004/0178586 A1 | 9/2004 | Junge |
| 2011/0264105 A1 | 10/2011 | Barthold |
| 2012/0238958 A1 | 9/2012 | Moore |
| 2012/0310166 A1 | 12/2012 | Huff |

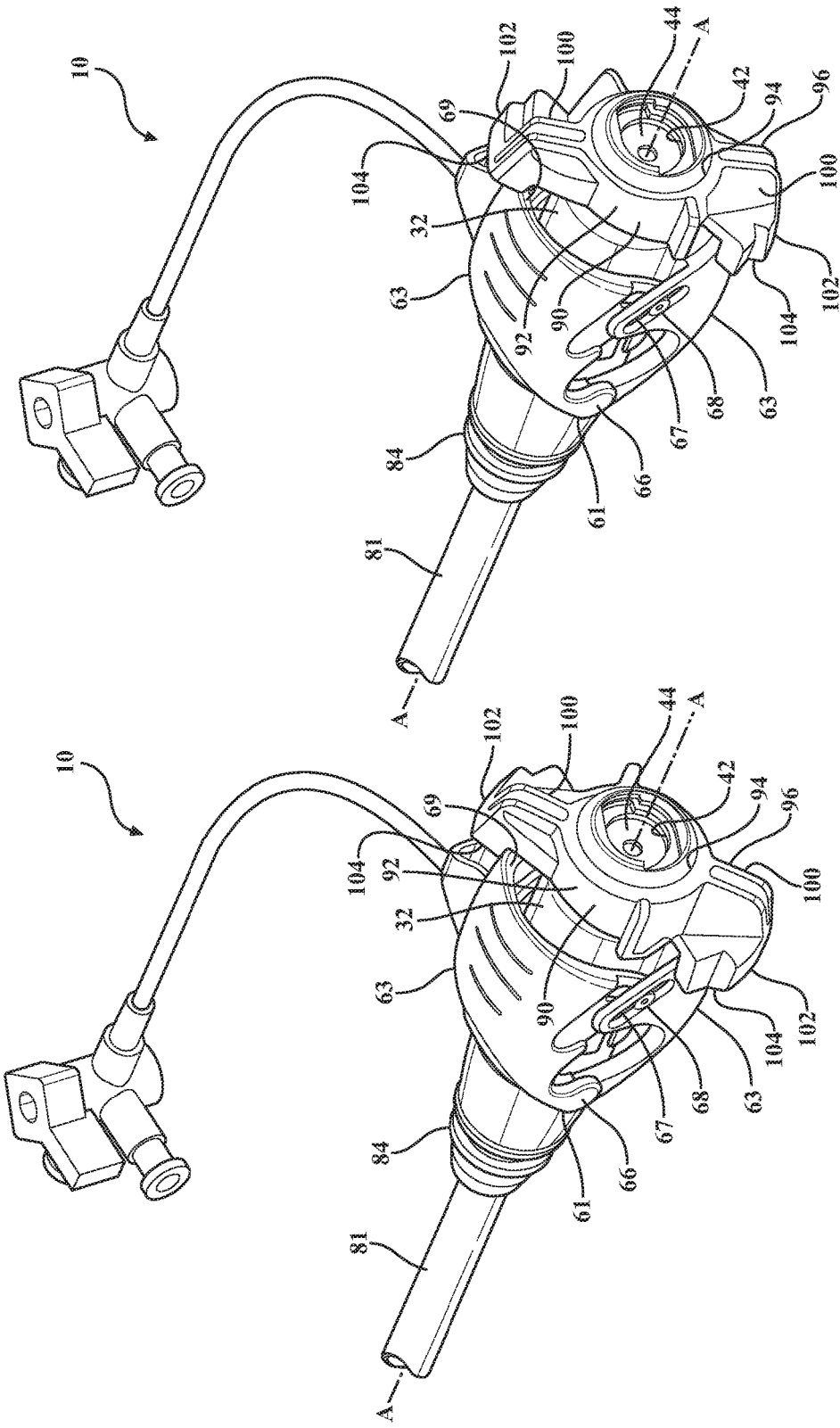

MEDICAL VALVE WITH A VARIABLE DIAMETER SEAL

CROSS-REFERENCE TO RELATED APPLICATIONS

This application is a continuation-in-part of U.S. patent application Ser. No. 15/483,089 filed on Apr. 10, 2017, which is a continuation of U.S. patent application Ser. No. 14/326,593, now U.S. Pat. No. 9,616,213, filed on Jul. 9, 2014. The entire disclosures of the above applications are incorporated herein by reference.

BACKGROUND OF THE INVENTION

1. Field of the Invention

The present disclosure relates generally to medical devices and procedures. In particular, the present disclosure relates to hemostatic valves and systems, and methods of using the same.

2. Description of the Prior Art

This section provides background information related to the present disclosure which is not necessarily prior art.

Numerous procedures have been developed that involve the percutaneous insertion of a medical device into a body vessel of a patient, with the medical device being introduced into the vessel by a variety of known techniques. Each of these procedures must control the flow of bodily fluids when the medical device is inserted into the body vessel. Accordingly, medical valves, such as hemostatic valves, iris valves, laproscopic ports, or the like, are often used to limit or prevent blood loss during the procedure.

Hemostatic valves often incorporate a disk valve to control fluid flow through the medical device. However, disk valves are subject to deformation with both time and use, and often can tear or become dislodged during insertion and/or withdrawal of the medical device. Furthermore, disk valves are not designed to provide an effective seal across a wide range of differently sized medical devices. Although the disk valve can be modified to accommodate these situations, such as with increased tensile and/or elongation properties, this modification leads to increased resistance, and thus require the use of excessive force, when the medical device is inserted and withdrawn through the disk valve.

Iris valves can include an elastomeric sleeve that is disposed within a valve body and which is interconnected to a rotatable cap. When the cap is rotated in a first direction, an opening extending through the elastomeric sleeve is opened. Conversely, when the cap is rotated in a second opposite direction, the elastomeric sleeve is twisted and constricted to effectuate a closure of the elastomeric sleeve. However, if the operator stops the rotation, the elastomeric sleeve can revert, or recoil, back to the open position. Additionally, even when the elastomeric sleeve is held in the closed position, gaps or channels extend therethrough as a result of the twisting or infolding required to effectuate a closure. Accordingly, fluid can leak through the iris valve in the closed position. Further, the continuous twisting and constricting of the elastomeric sleeve leads to wear of the sleeve, such as through tearing.

The drawbacks associated with the existing medical valves are further exemplified when one considers that a single medical valve often is used to insert multiple medical devices during a single procedure. For example, a hemostatic valve may be used first for introducing a delivery catheter, followed by an interventional catheter. In this example, the hemostatic valve must be able to provide a hemostatic seal under a variety of conditions, i.e., accommodate a variety of different sized medical devices. Additionally, the hemostatic valve device must be able to quickly adjust to use of each of these different medical devices, otherwise significant fluid loss can occur through the medical valve.

SUMMARY OF THE INVENTION

This section provides a general summary of the disclosure and is not intended to be a comprehensive disclosure of its full scope, aspects, objectives, and/or all of its features.

A medical valve assembly for use in inserting a medical device into a body vessel of a patient includes a tube extending between a first tube end and a second tube end to define a passageway extending longitudinally along an axis between the ends. A plunger plate extends radially from the second tube end and a valve housing surrounds the tube about the second tube end. The valve housing extends from a first valve housing end to a second valve housing end and includes a housing flange extending radially inwardly from the second valve housing end, with the housing flange disposed in spaced relationship with respect to the plunger plate so as to define a distance dimension therebetween. An elastomeric seal is compressed between the plunger plate and the housing flange and has an inner diameter for use in establishing a variable seal of the medical valve assembly. A compression member is disposed within the valve housing and is biased against the plunger plate for decreasing the inner diameter to establish a closed inner diameter of the elastomeric seal and a respective closed condition of the medical valve assembly. A pair of lever arms are pivotably connected to the valve housing and radially compressible to overcome the bias of the compression member and effectuate axial movement of the valve housing relative to the tub to increase the distance between the plunger plate and the housing flange and increase the inner diameter of the elastomeric seal from the closed condition. A locking ring is rotatably connected to the second valve housing end and is rotatable relative to the pair of lever arms to establish and maintain a radially compressed condition of the pair of lever arms and a respective increased inner diameter of the elasteromic seal. As a result, the locking ring allows a user of the medical valve assembly to establish and maintain the increased inner diameter of the elastomeric seal during use without the need for the user to constantly maintain a manual radial compression on the pair of lever arms. Thus, the locking ring improves the user experience during use of the medical valve assembly.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments, and are not all possible implementations and thus are not intended to limit the scope of the present disclosure.

FIG. 17 is a perspective view of the medical valve illustrating the second arrangement of the locking ring disposed in a first intermediate position;

FIG. 19 is a perspective view of the medical valve illustrating the second arrangement of the locking ring disposed in a second intermediate position;

DESCRIPTION OF THE ENABLING EMBODIMENTS

Example embodiments will now be described more fully with reference to the accompanying drawings. The example embodiments are provided so that this disclosure will be thorough and fully convey the scope to those skilled in the art. Numerous specific details are set forth such as examples of specific components, devices, mechanisms, assemblies, and methods to provide a thorough understanding of various embodiments of the present disclosure. It will be apparent to those skilled in the art that specific details need not be employed, that example embodiments may be embodied in many different forms, and that neither should be construed to limit the scope of the disclosure. With this in mind, the present disclosure is generally directed to medical valve assemblies of the type used to introduce and withdrawal a medical device (i.e., a guide wire, catheter, stent, filter, etc.) into a body vessel of a patient. In particular, each of the medical valve assemblies of the present disclosure incorporate a variable seal arrangement and a manually-operable actuator for controlling an entry dimension of the variable seal arrangement.

Figure 1:
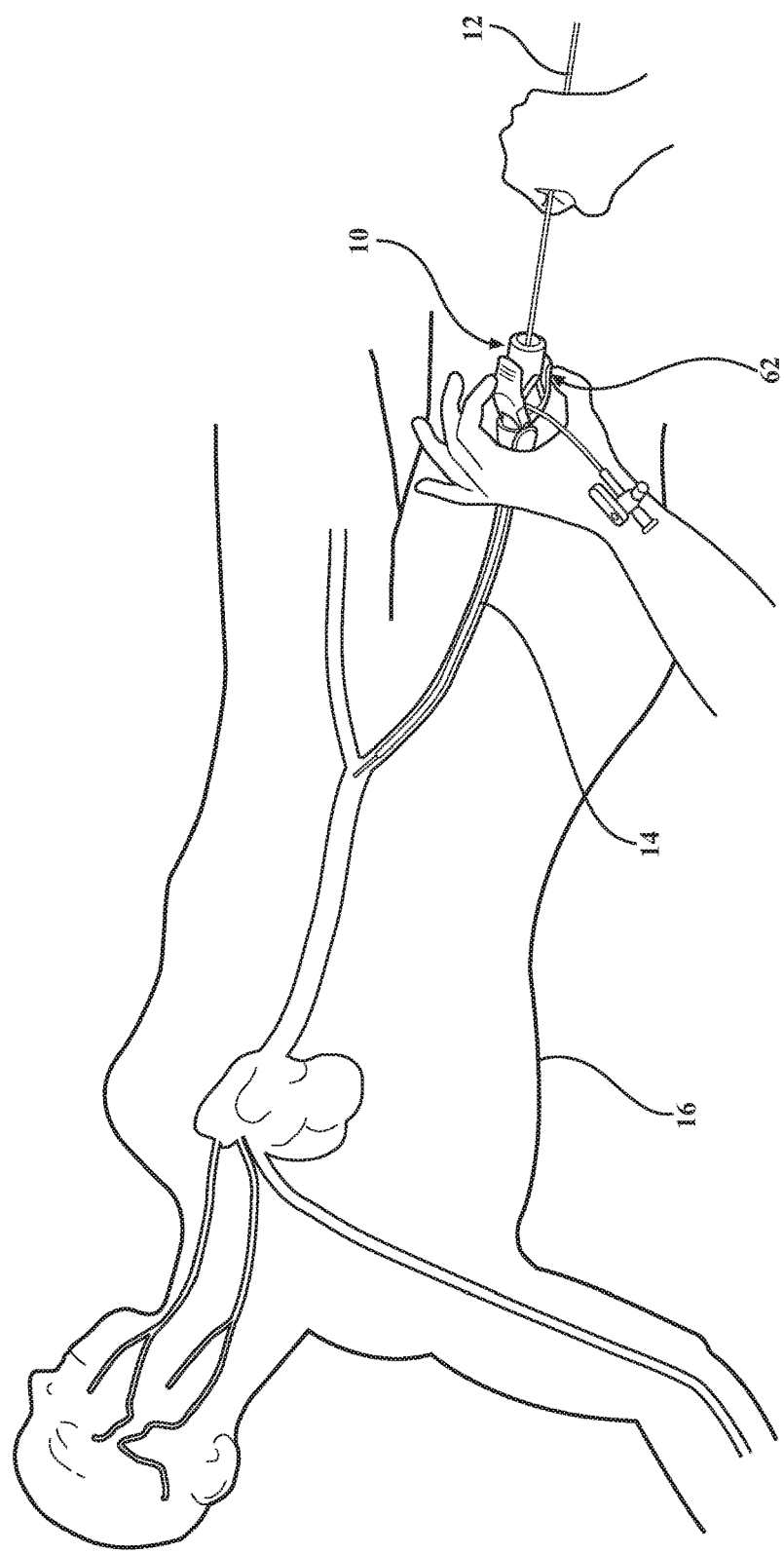
FIG. 1 is an environmental view of a first embodiment of a medical valve constructed in accordance with the principles of the present disclosure and illustrating a user interacting therewith.
Figure 2:
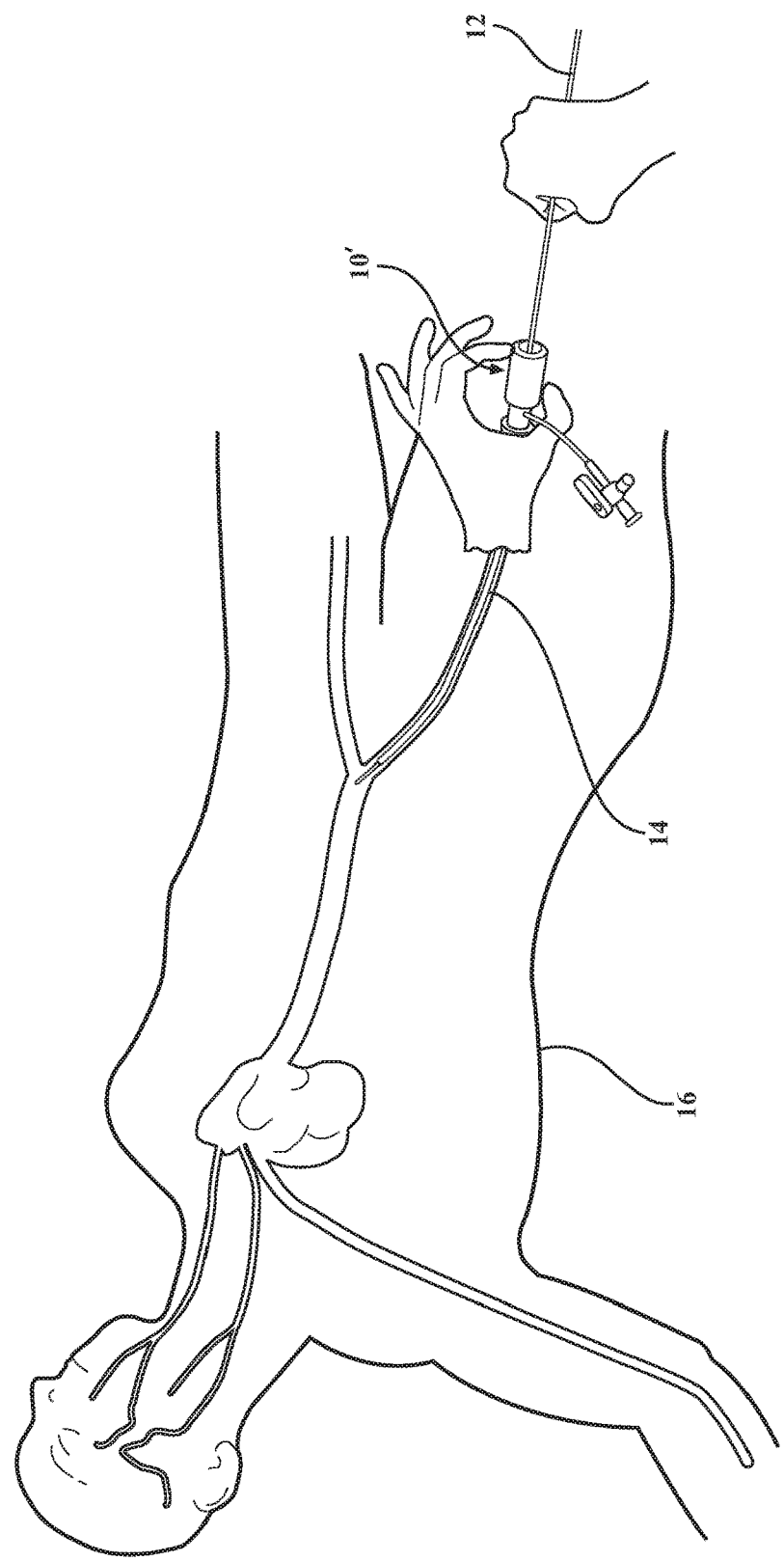
FIG. 2 is an environmental view of a second embodiment of the medical valve constructed in accordance with the principles of the present disclosure and illustrating the user interacting therewith.

Referring to the Figures, wherein like numerals indicate corresponding parts throughout the several views, an environmental view of a first embodiment of a medical valve assembly 10 and a second embodiment of a medical valve assembly 10' is generally shown in FIGS. 1 and 2, respectively. As illustrated therein, each medical valve assembly 10, 10' is of the type for use with a medical device 12, such as a guide wire, catheter, stent, filter, vessel occlusion device, or the like. As will be explained in more detail below, as the medical device 12 is inserted and guided through the medical valve assembly and into a body vessel 14 of a patient 16, a user can manually actuate or interact with the medical valve assembly to effectuate a variable seal with variety of different sized medical devices 12.

Figure 4A:
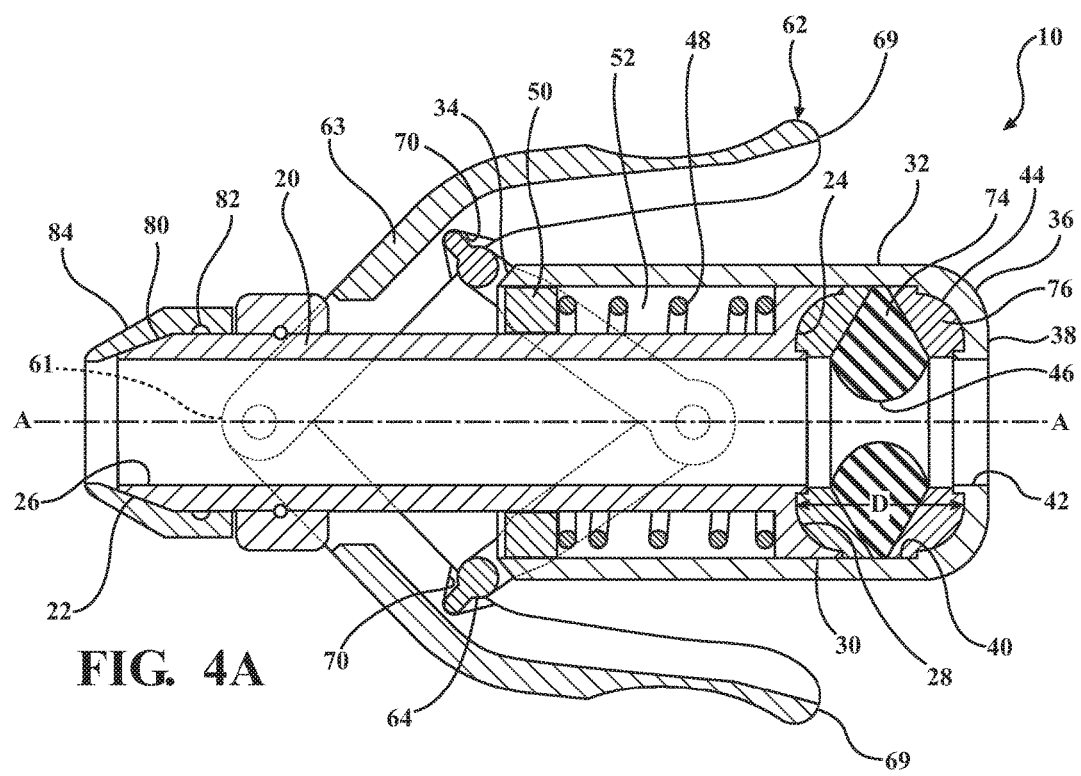
FIG. 4A is a cross-sectional view of the first embodiment of the medical valve illustrating a closed condition.
Figures 4B, 5:
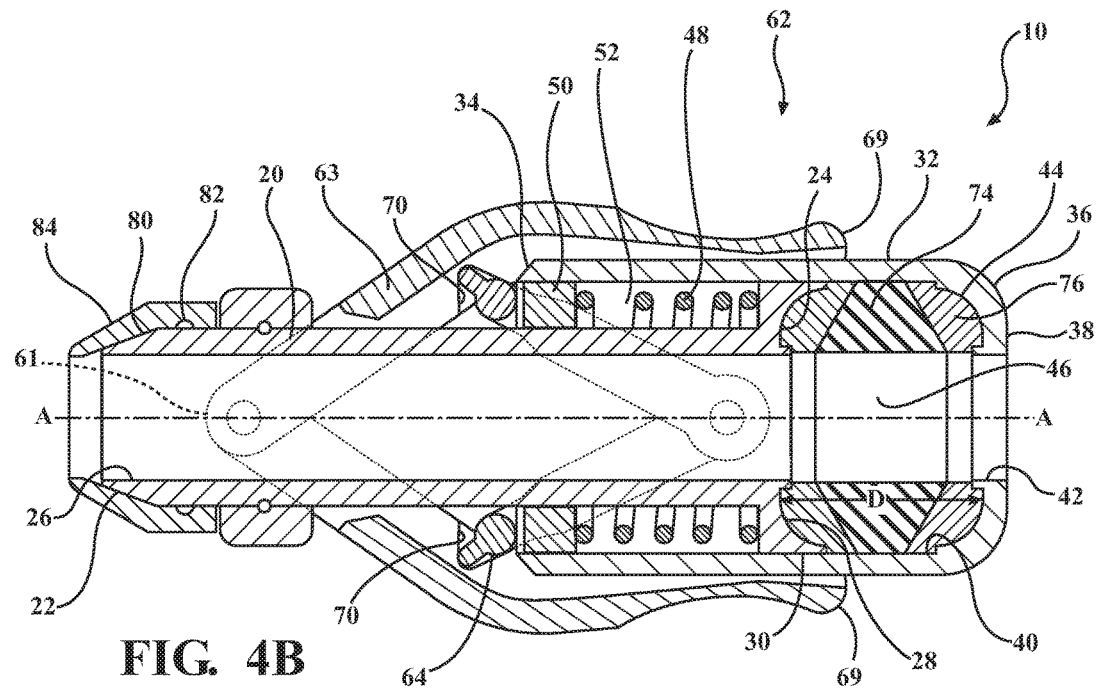
FIG. 4B is a cross-sectional view of the first embodiment of the medical valve illustrating an open condition.
FIG. 5 is a partial view taken from FIG. 3 illustrating an elastomeric seal of the medical valve.
Figure 9:
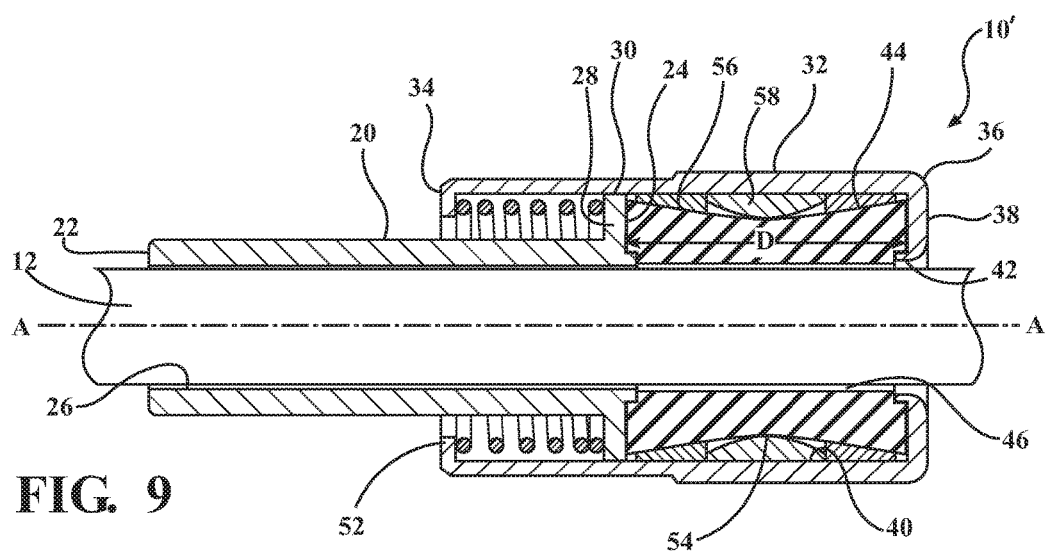
FIG. 9 is a cross-sectional view of the second embodiment shown in FIG. 8.

As best shown in FIGS. 4A, 4B and 9, the medical valve assemblies 10, 10' each include a tube 20 extending between a first tube end 22 and a second tube end 24 to define a passageway 26 extending longitudinally along an axis A between the ends 22, 24, with the passageway 26 being sized to receive a variety of differently sized medical devices 12. In this instance, the first tube end 22 is a distal tube end and the second tube end is a proximal tube end 24. A plunger plate 28 extends radially from the second tube end 24 to define an outer plunger plate surface 30 extending in spaced and parallel relationship to the axis A. A valve housing 32 is disposed in surrounding relationship with the tube 20 about the second tube end 24 and extends from a first valve housing end 34 to a second valve housing end 36 to overlay the outer plunger plate surface 30. In this instance, the first valve housing end 34 is a distal valve housing end and the second valve housing end 36 is a proximal valve housing end 36. As best shown in FIGS. 4A, 4B and 9, the valve housing 32 is disposed in spaced and parallel relationship with the tube 20 between the first valve housing end 34 and the plunger plate 28.

The valve housing 32 includes a housing flange 38 extending radially inwardly from the second valve housing end 36. The housing flange 38 is disposed in spaced relationship with the plunger plate 28 to define a distance dimension D, as well as a cavity 40, extending therebetween. The housing flange 38 also defines an opening 42 aligned on the axis A and that is sized to receive a variety of differently sized medical devices 12. An elastomeric seal 44 is installed in the cavity 40 and normally is pre-loaded or compressed between the plunger plate 28 and the housing flange 38. The elastomeric seal 44 is used to establish a variable seal of the medical valve assembly 10, 10'. In both of the first and second embodiments of the medical valve assembly 10, 10', one of the valve housing 32 or the tube 20 is axially movable relative to the other to vary the distance dimension D between the plunger plate 28 and the housing flange 38 for effectuating an adjustment of an inner diameter 46 of the elastomeric seal 44. In other words, the axial movement of one of the valve housing 32 or the tube 20 relative to the other results in a change in the compression load exerted on the elastomeric seal 44 which, in turn, allows the inner diameter 46 of the elastomeric seal 44 to be varied or adjusted in size. As best shown in FIGS. 4A, 4B and 9, when the valve housing 32 or the tube 20 is axially moved, the plunger plate 28 or the valve housing 32 axially slides relative to the other along the outer plunger plate surface 30. In other words, the outer plunger plate surface 30 guides a sliding axial movement between the valve housing 32 and the tube 20.

As best shown in FIGS. 4A, 4B, and 9, a compression member 48, 54 is disposed within the valve housing 32 and is compressed against the plunger plate 28 for normally closing or decreasing the inner diameter 46 to establish a closed position of the elastomeric seal 44. As a result, the compression member 48, 54 is arranged to effectuate a closing or decreasing of the inner diameter 46 of the elastomeric seal 44 to establish a closed condition of the medical valve assembly 10, 10'. In its closed condition, the elastomeric seal 44 completely isolates or seals the opening 42 of the valve housing 32 from the passageway 26 of the tube 20. The valve housing 32 or the tube 20 is then axially movable relative to the other to alter a distance D between the housing flange 38 and the plunger plate 28 and shift the medical valve assembly 10, 10' from the closed condition to an open/operative condition. The altered or varied distance D between the housing flange 38 and the plunger plate 28 allows the elastomeric seal 44 to expand, and as a result, the inner diameter 46 of the elastomeric seal 44 is expanded or increased to move the elastomeric seal 44 from its closed position to an open position. With the elastomeric seal 44 in its open position, the medical device 12 is positioned to be inserted serially through the opening 42, the inner diameter 46 of the elastomeric seal 44 and the passageway 26 of the medical valve assembly 10.

As best shown in FIGS. 4A and 4B, in the first embodiment of medical valve assembly 10, the compression member 48, 54 comprises a coil spring 48 radially disposed between the valve housing 32 and the tube 20 and compressed between the first valve housing end 34 and the plunger plate 28. However, any other suitable compression member could be utilized without departing from the scope of the subject disclosure. In a preferred embodiment, a disk 50 is slidably disposed around the tube 20 and interconnected to the first valve housing end 34 to establish a shoulder 52 extending radially inward from the valve housing 32 and which is disposed in engagement with the coil spring 48. The coil spring 48 acts to bias the valve housing 32 towards the first tube end 22 for compressing the elastomeric seal 44 between the housing flange 38 and the plunger plate 28 and normally position the elastomeric seal 44 in its closed position. The valve housing 32 is then axially movable from the closed position and relative to the tube 20 to increase the distance D between the housing flange 38 and the plunger plate 28. The increased distance D allows the elastomeric seal 44 to expand in an increased area of the cavity 40 disposed between the housing flange 38 and the plunger plate 28, and as a result, the inner diameter 46 of the elastomeric seal 44 is expanded or increased, thereby opening the elastomeric seal 44. The result is the establishment of the open condition of the medical valve assembly 10.

Figure 8:
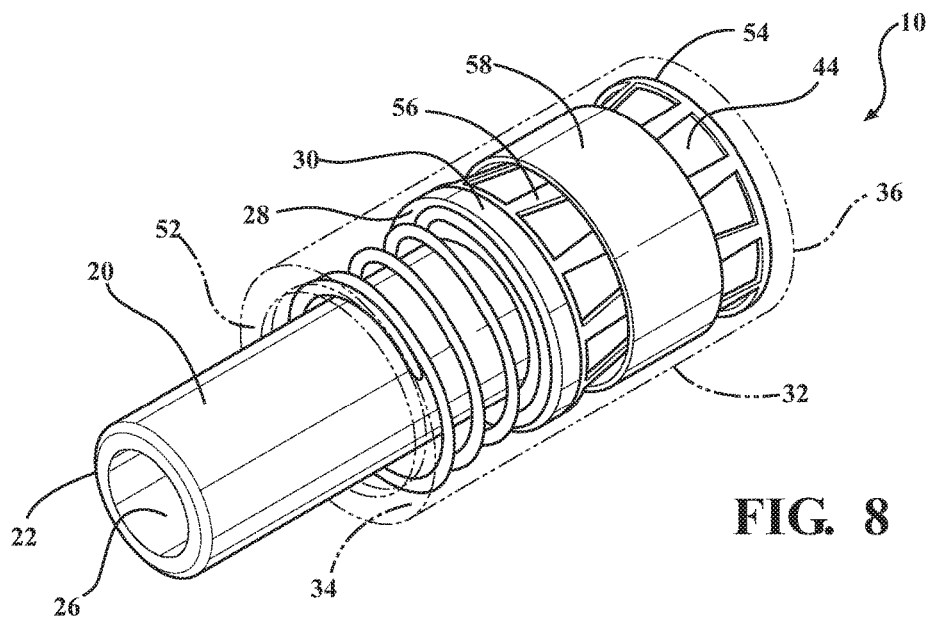
FIG. 8 is a perspective view of the second embodiment of a medical valve constructed in accordance with the present disclosure.

As best shown in FIGS. 8 and 9, in the second embodiment of the medical valve assembly 10', the compression member 48, 54 also comprises a coil spring 48 radially disposed between the valve housing 32 and the tube 20 and compressed between the first valve housing end 34 and the plunger plate 28. However, any other suitable compression member could be utilized without departing from the scope of the subject disclosure. The valve housing 32 defines a shoulder 52 extending radially inward from the first valve housing end 34 and slidably disposed around the tube 20. The shoulder 52 is disposed in engagement with the coil spring 48, and the coil spring 48 acts to bias the valve housing 36 towards the first tube end 22. In a preferred embodiment, the compression member 48, 54 additionally includes a leaf spring cage 54 disposed in surrounding relationship with the elastomeric seal 44. However, any other suitable compression member could be utilized without departing from the scope of the subject disclosure. The leaf spring cage 54 extends between the plunger plate 28 and the housing flange 38 and is compressed therebetween by way of the compression spring 48. The leaf spring cage 54 includes a plurality of struts 56 each extending axially along the leaf spring cage 54 and configured to fold radially inward towards the elastomeric seal 44 when the valve housing 36 is axially biased towards the first tube end 22 by the compression spring 48. As a result, the distance D between the plunger plate 28 and the housing flange 38 is decreased, thus causing the elastomeric seal 44 to compress and reduce the inner diameter 46. Put another way, the coil spring 48 and the leaf spring cage 54 interact to compress the elastomeric seal 44 between the housing flange 38 and the plunger plate 28 and normally position the elastomeric seal 44 in its closed position. As a medical device 12 is inserted through the passageway 26, the medical device 12 engages the elastomeric seal 44 with an insertion force that is transferred or exerted radially outward on the struts 56 of the leaf spring cage 54, causing the leaf spring cage 54 to expand and counteract the biasing force of the coil spring 48. As a result, the distance between the plunger plate 28 and the housing flange 38 is increased, allowing the inner diameter 46 of the elastomeric seal 44 to expand or increase and establish the open condition of the medical valve assembly 10'. A constrictor band 58 extends around the leaf spring cage 54 to prevent the plurality of struts 56 from engaging the valve housing 32 when the leaf spring cage 54 is expanded by the insertion force of the medical device 12.

Figure 3:
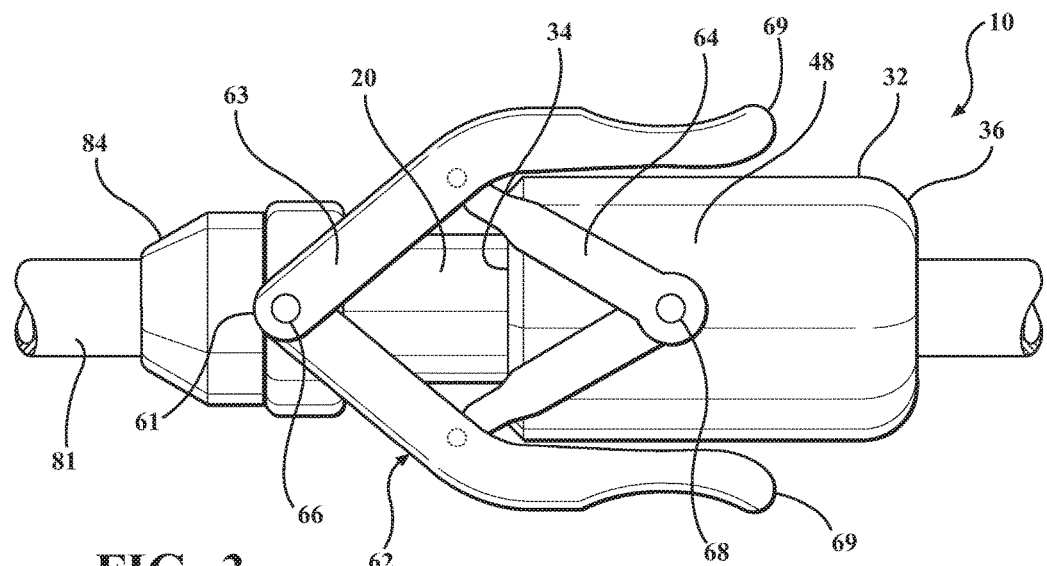
FIG. 3 is a perspective view of the first embodiment of the medical valve illustrating a scissor-type manual actuator.
Figure 6:
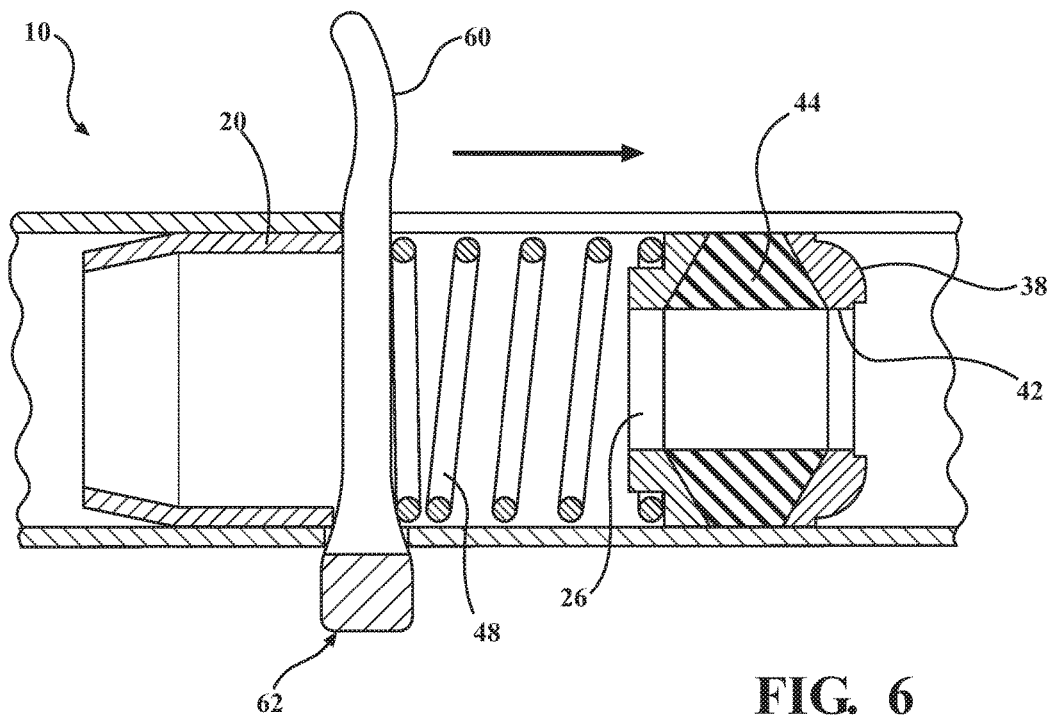
FIG. 6 is a cross-sectional view of the first embodiment of the medical valve illustrating an alternative arrangement for the manual actuator.

As best shown in FIGS. 3, 4A, and 4B, the first embodiment of the medical valve assembly 10 includes a manual actuator 62 which can be connected to the valve housing 32 for allowing a user to interact with the medical valve assembly 10 and vary a size of the inner diameter 46 of the elastomeric seal 44. Put another way, the user can interact with the manual actuator 62 to overcome the bias of the compression member 48 and move the valve housing 32 relative to the tube 20 along the axis A towards the second tube end 24. As a result, the manual actuator 62 allows the user to manually establish the open condition of the medical valve assembly 10. As best shown in FIG. 6, in the alternative embodiment, the manual actuator 62 can include a trigger arm 60 extending radially from the valve housing 32. In this situation, the user can pull back on the trigger arm 60 to establish the open condition of the medical valve assembly 10. In other words, a user can pull back the trigger arm 60 to vary the bias on the plunger plate 28.

Figure 7:
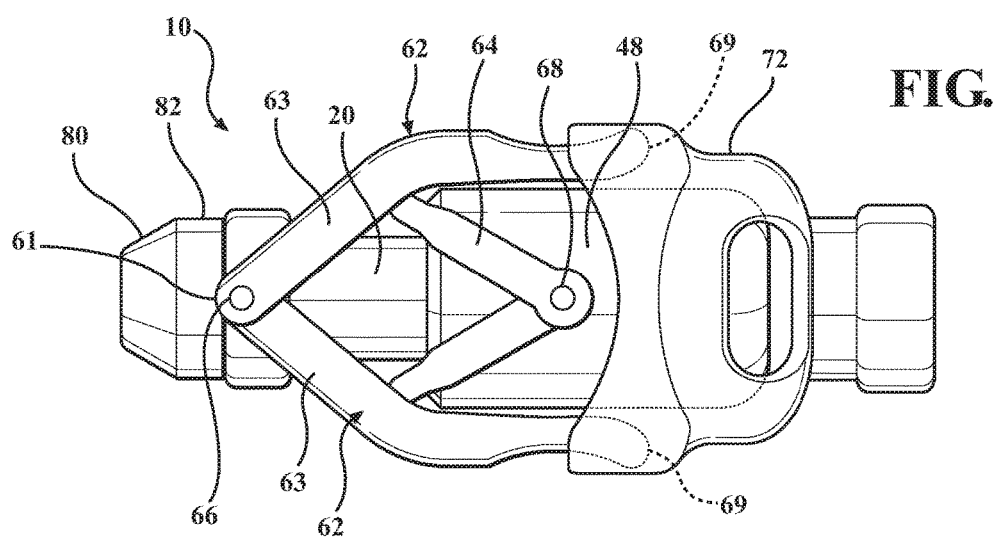
FIG. 7 is a perspective view of the first embodiment illustrating a detachable cap disposed over a pair of lever arms associated with the scissor-type manual actuator.

As best shown in FIGS. 3 and 4, the manual actuator 62 can include a pair of lever arms 63 interconnected between the tube 20 and the valve housing 32 by way of a pair of lever linkages 64. As best shown in FIG. 3, each lever arm 63 extends from a first lever arm end 61 pivotably connected to the tube 20 via a first pivot 66 extending radially from the tube 20 to a second lever arm end 69 having an arcuate shape relative to said axis A. Each lever linkage 64 includes a second pivot 68 extending radially from the valve housing 32. The pair of lever linkages 64 are pivotably connected to the valve housing by the second pivots 68 with each of the lever linkages 64 extending from the respective second pivot 68 to engage one of the respective lever arms 63. As best shown in FIG. 7, in a preferred embodiment, each of the lever arms 63 can also define a track 70 for receipt of the respective lever linkage 64 when the lever linkages 64 are disposed in abutting relationship with the lever arms 63. This arrangement of the lever arms 63 and the lever linkages 64 allows the user to squeeze or compress the pair of lever arms 63 with a specific force to axially advance the valve housing 32 by way of the lever linkages 64. As a result, the transferred force effectuates the increase in the distance D between the plunger plate 28 and the housing flange 38, and thus the increase in the inner diameter 46 of the elastomeric seal 44. Put another way, a user can radially squeeze or compress the lever arms 63 to release compression on the elastomeric seal 44 and increase the inner diameter 46 of the elastomeric seal 44 from the closed condition to a desired size of the inner diameter 46 based on an amount of radial squeeze.

Figure 10:
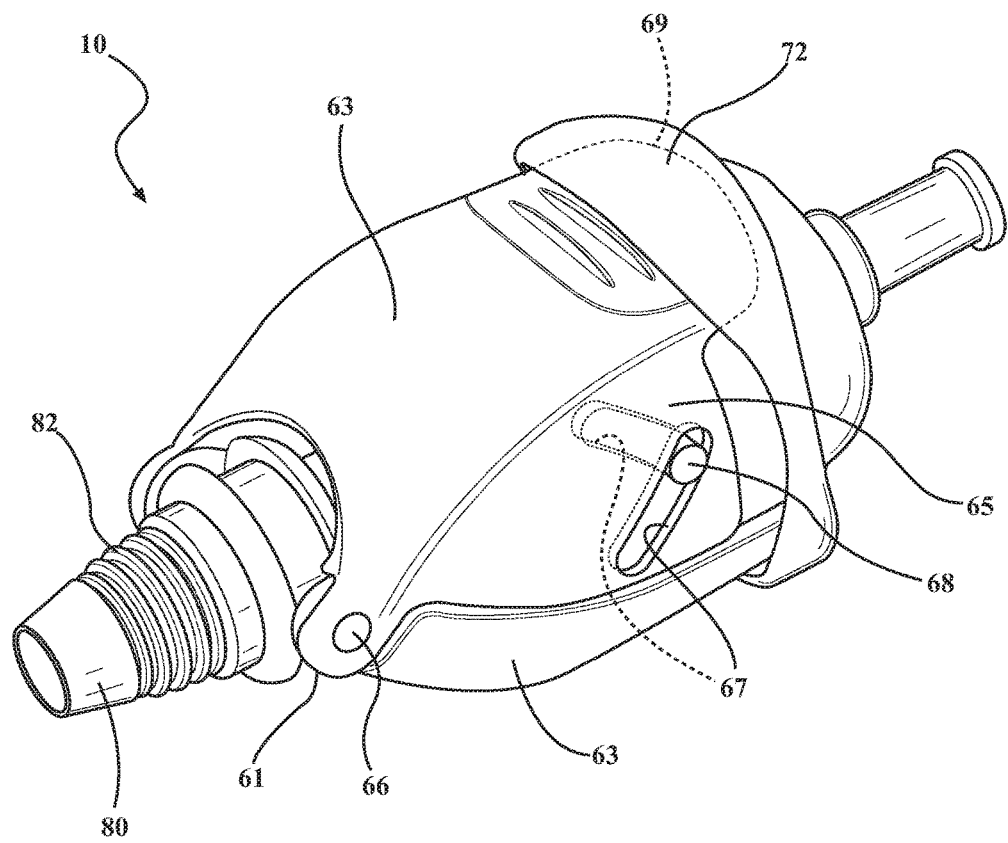
FIG. 10 is a perspective view of the first embodiment illustrating an alternative arrangement of the scissor-type manual actuator.
Figure 11:
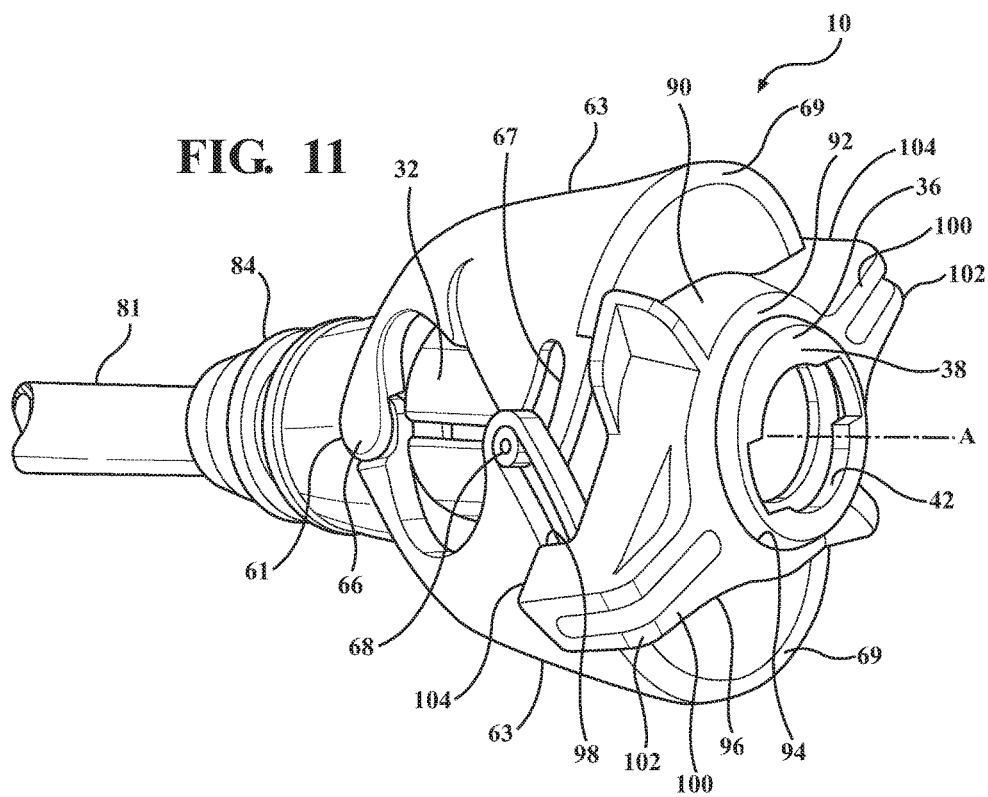
FIG. 11 is a perspective view of a medical valve illustrating a first arrangement of a locking ring in accordance with the principles of the present disclosure and disposed in a first, closed position.

As best shown in FIG. 10, in an alternative arrangement the pair of lever arms 63 can be interconnected between the tube 20 and the valve housing 32 by way of a pair of plates 65. In a preferred embodiment, each lever arm 63 includes a plate 65 which extends radially therefrom and which defines a cam slot 67 for receiving the second pivot 68 extending radially from the valve housing 32. This arrangement of the lever arms 63 and the plates 65 allows the user to squeeze or compress the pair of lever arms 63 with a specific force to slide the second pivot 68 along the cam slots 67 and axially advance the valve housing 32 by way of the plates 65. As a result, the transferred force effectuates the increase in the distance D between the plunger plate 28 and the housing flange 38, and thus the increase in the inner diameter 46 of the elastomeric seal 44. Put another way, a user can radially squeeze or compress the lever arms 63 to release compression on the elastomeric seal 44 and increase the inner diameter 46 of the elastomeric seal 44 from the closed condition to a desired size of the inner diameter 46 based on an amount of radial squeeze.

As best shown in FIG. 7, a detachable cap 72 can be snapped or disposed over the second valve housing end 36 of the valve housing 32 to hold the pair of lever arms 63 in the radially compressed position when the medical valve assembly 10 is not in use. When the detachable cap 72 is in place, it keeps the elastomeric seal 44 in the open position, and thus increases the shelf life by reducing material creep, material sticking, and/or the distorting of the elastomeric seal 44. However, as best shown in FIGS. 11-27, in an alternative arrangement a locking ring 90 can be rotatably connected to the second valve housing end 36 and rotatable relative to the pair of lever arms 63 to establish and maintain a radially compressed condition of the pair of lever arms 63 and an increased inner diameter 46 of the elastomeric seal 44. Similar to the detachable cap 72, the locking ring 90 can also be set to advantageously hold the pair of lever arms 63 in the radially compressed position without user intervention when the medical valve assembly 10 is not in use to keep the elastomeric seal 44 in the open position, and thus increase the shelf life by reducing material creep, material sticking, and/or the distorting of the elastomeric seal 44. Additionally, as will be explained in more detail below, the locking ring 90 also allows a user of the medical valve assembly 10 to place and maintain the elastomeric seal in the open condition, or a plurality of other positions, during use of the medical valve assembly 10 for allowing a user to insert a medical device 12 therethrough without the need for the user to constantly maintain a manual radial compression on the pair of lever arms. Thus, the locking ring 90 also improves the user experience during use of the medical valve assembly 10.

The locking ring 90 is rotatable from a first, closed position (as best shown in FIGS. 11-12, 15, and 24), wherein the locking ring 90 is disposed in spaced and non-engaging relationship with the pair of lever arms 63 to establish the closed condition of the elastomeric seal 44, to a second, open position (as best shown in FIGS. 13-14, 21-22B, and 26) wherein the locking ring 90 engages and completely or fully radially compresses the pair of lever arms 63 to establish and maintain an increased and open inner diameter $D_O$ of the elastomeric seal 44. As best shown in FIGS. 14, 22A, 22B, and 27, the open inner diameter $D_O$ of the elastomeric seal 44, as established and maintained by the locking ring 90, establishes a respective open condition of the medical valve assembly 10 for allowing a medical device 12 to pass therethrough.

Figure 12:
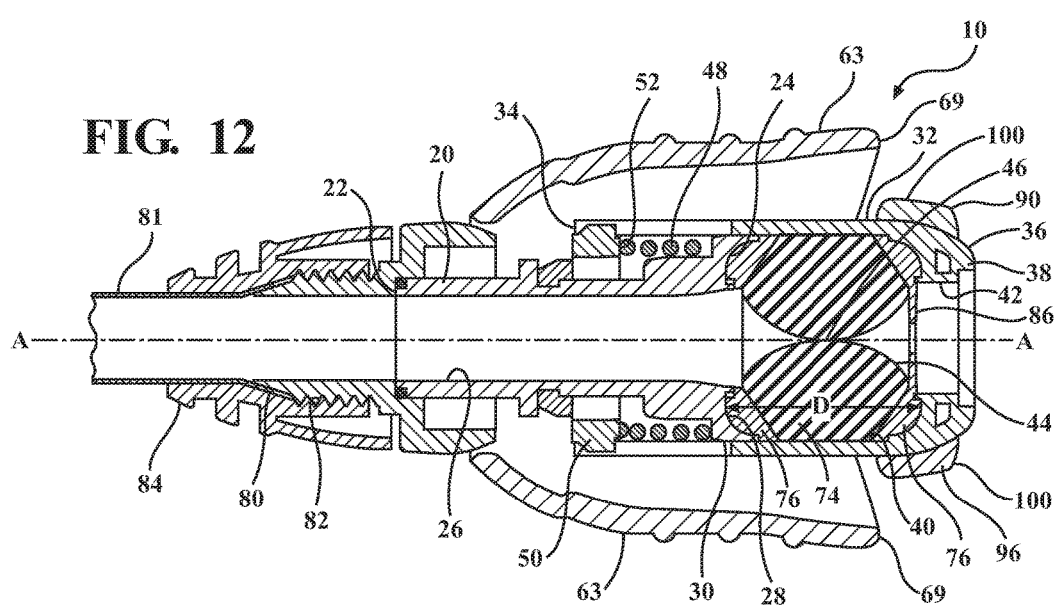
FIG. 12 is a cross-sectional view of the medical valve of FIG. 11.
Figure 13:
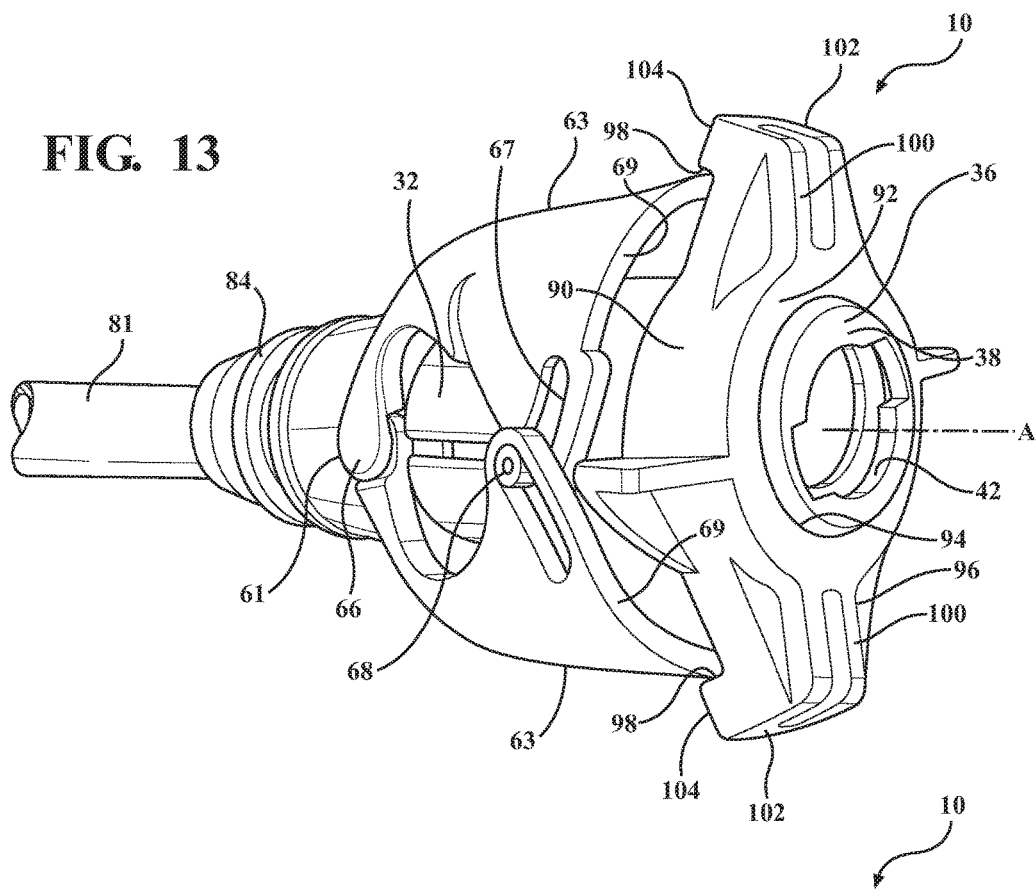
FIG. 13 is a perspective view of the medical valve illustrating the first arrangement of the locking ring disposed in the second, open position.
Figure 14:
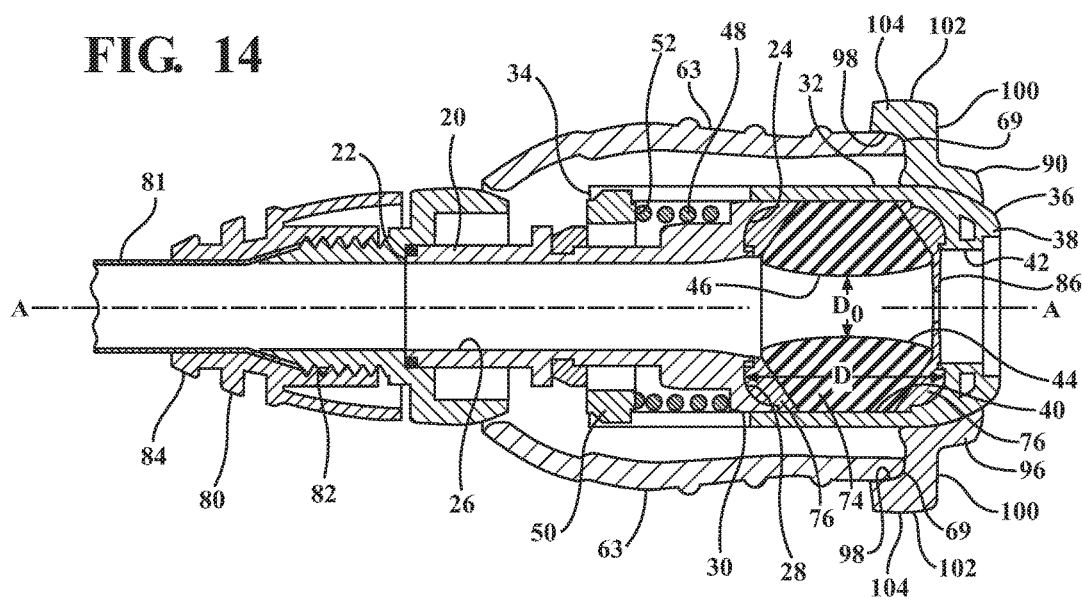
FIG. 14 is a cross-sectional view of the medical valve of FIG. 13.
Figure 16:
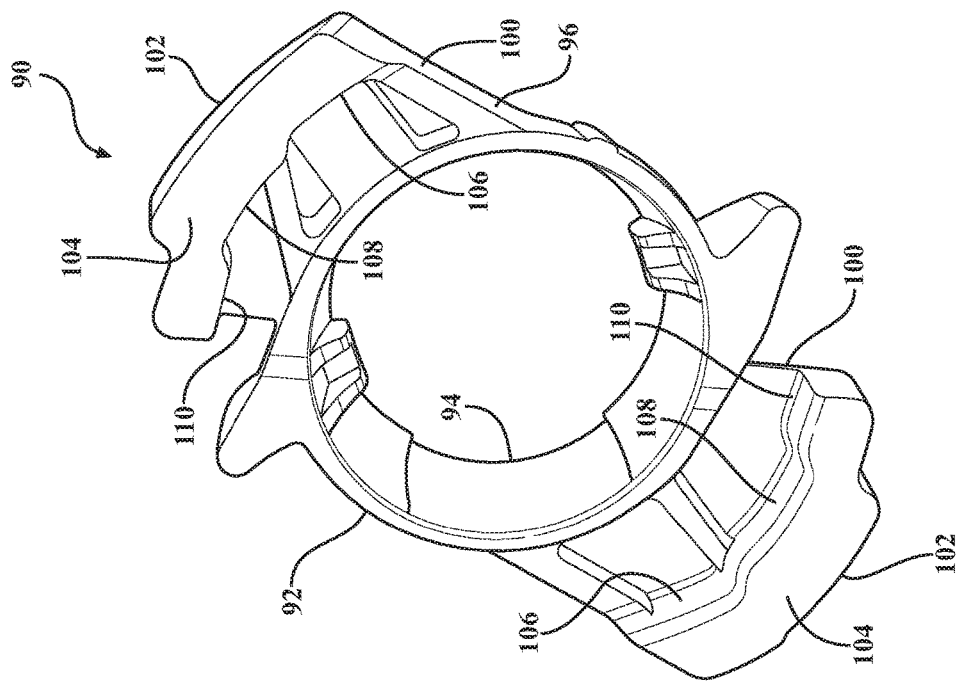
FIG. 16 is a perspective view of the second arrangement of the locking ring illustrating a pair of locking flanges each defining a locking surface that presents a plurality of steps.
Figure 15:
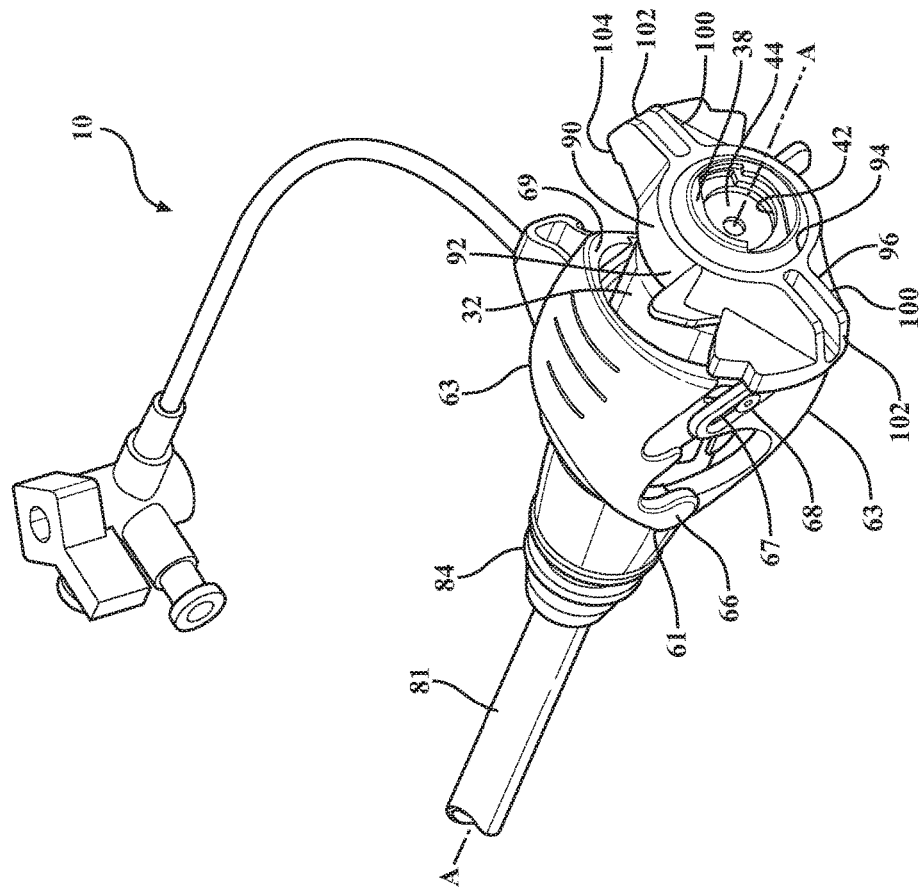
FIG. 15 is a perspective view of the medical valve illustrating a second arrangement of a locking ring in accordance with the principles of the present disclosure and disposed in a first, closed position.
Figures 18A, 18B:
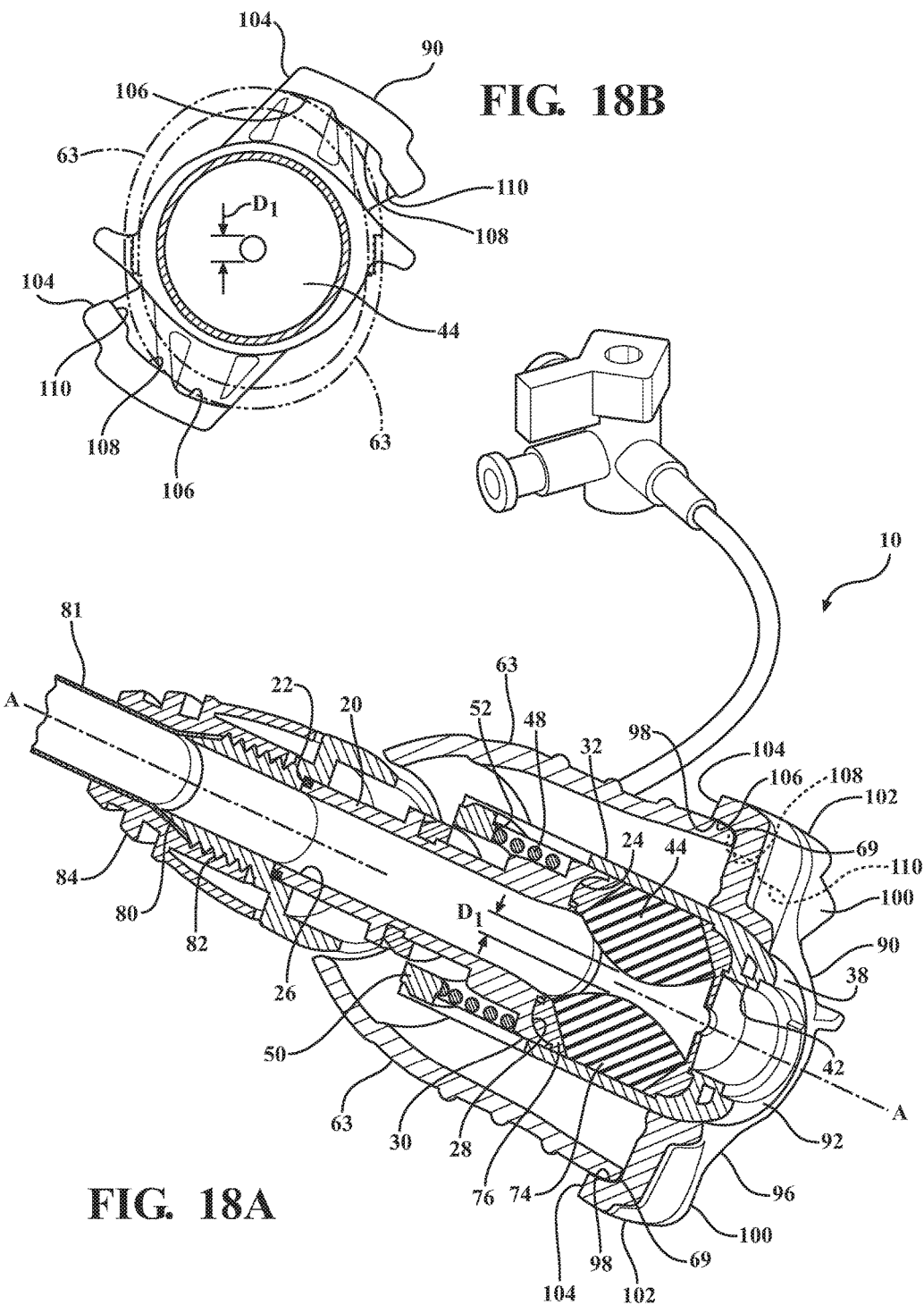
FIG. 18A is a cross-sectional perspective view of the medical valve of FIG. 17 illustrating a first intermediate inner diameter established and maintained by the first intermediate position of the locking ring.
FIG. 18B is a cross-sectional end view of the medical valve illustrating a first step of the plurality of steps disclosed in engaging relationship with a respective one of the lever arms in the first intermediate position of the locking ring.
Figure 20B:
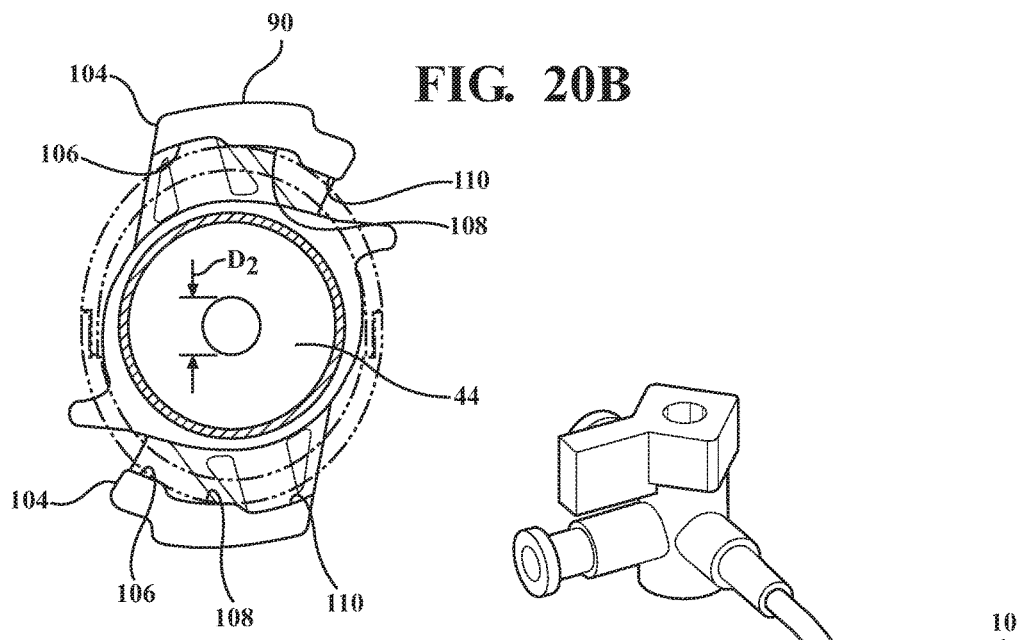
FIG. 20B is a cross-sectional end view of the medical valve illustrating a second step of the plurality of steps disclosed in engaging relationship with a respective one of the lever arms in the first intermediate position of the locking ring.
Figure 20A:
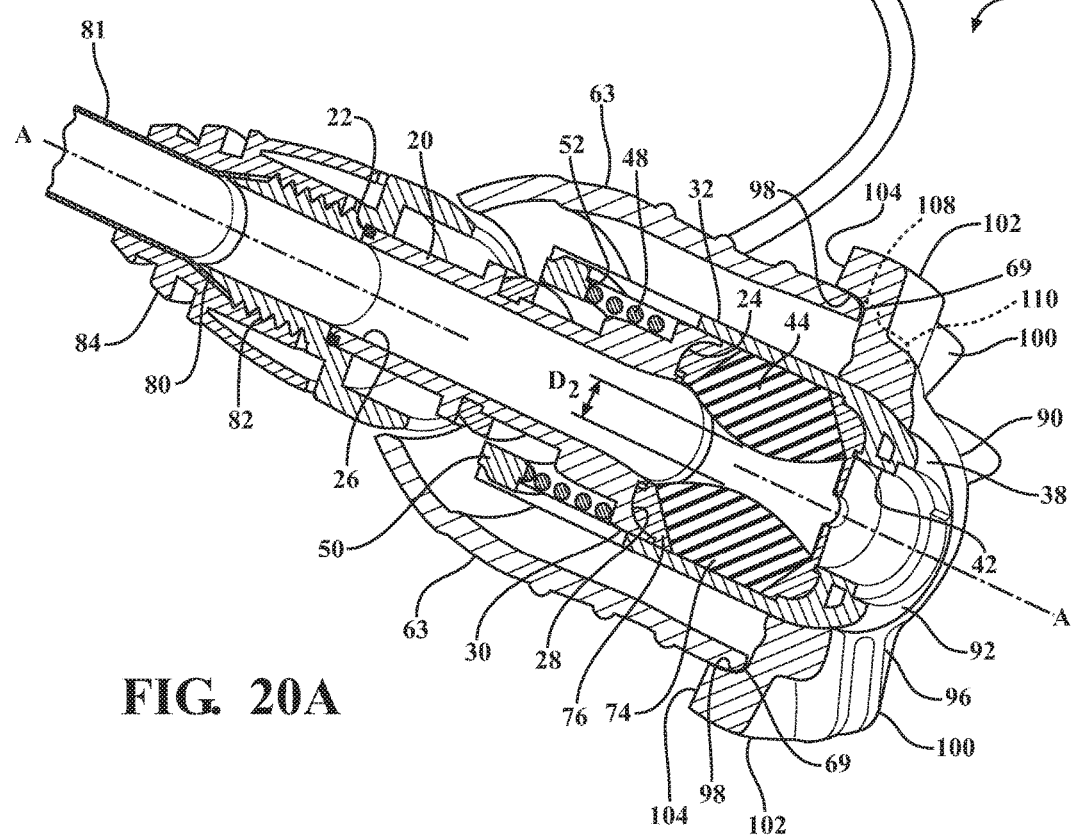
FIG. 20A is a cross-sectional perspective view of the medical valve of FIG. 19 illustrating a second intermediate inner diameter established and maintained by the second intermediate position of the locking ring.
Figure 21:
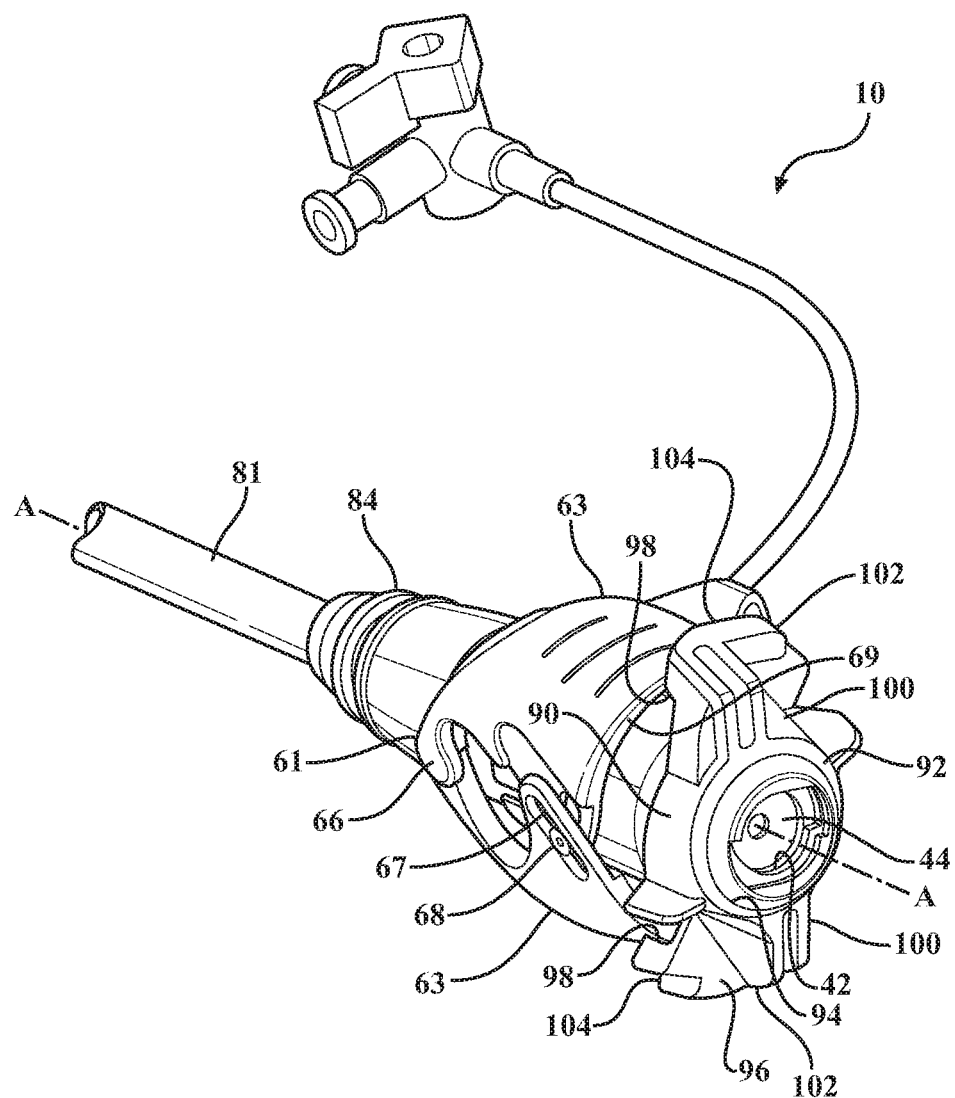
FIG. 21 is a perspective view of the medical valve illustrating the second arrangement of the locking ring disposed in the open position.
Figure 22:
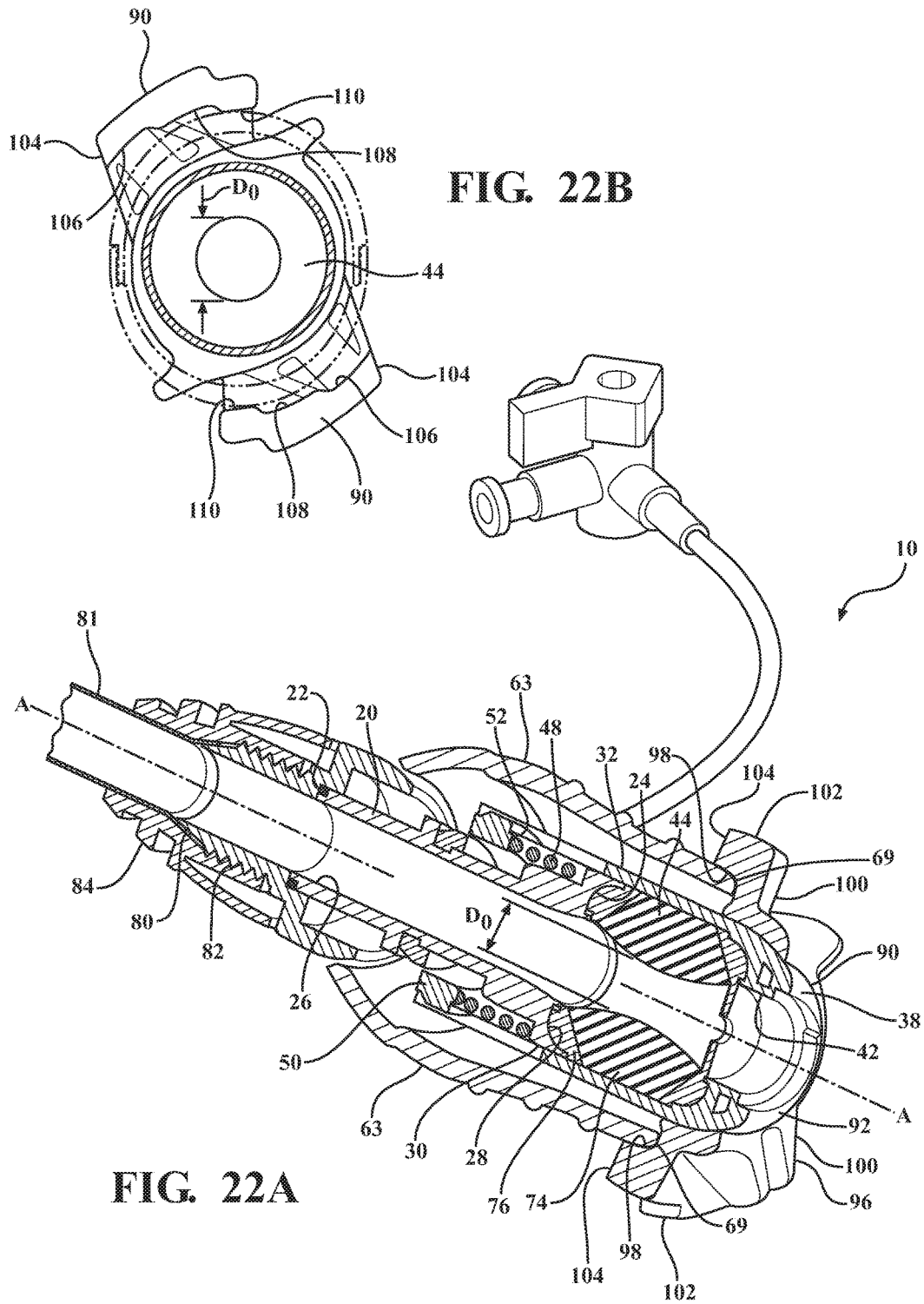
FIG. 22A is a cross-sectional perspective view of the medical valve of FIG. 21 illustrating an open inner diameter established and maintained by the open position.
FIG. 22B is a cross-sectional end view of the medical valve illustrating a third step of the plurality of steps disclosed in engaging relationship with a respective one of the lever arms in the open position of the locking ring.
Figure 23:
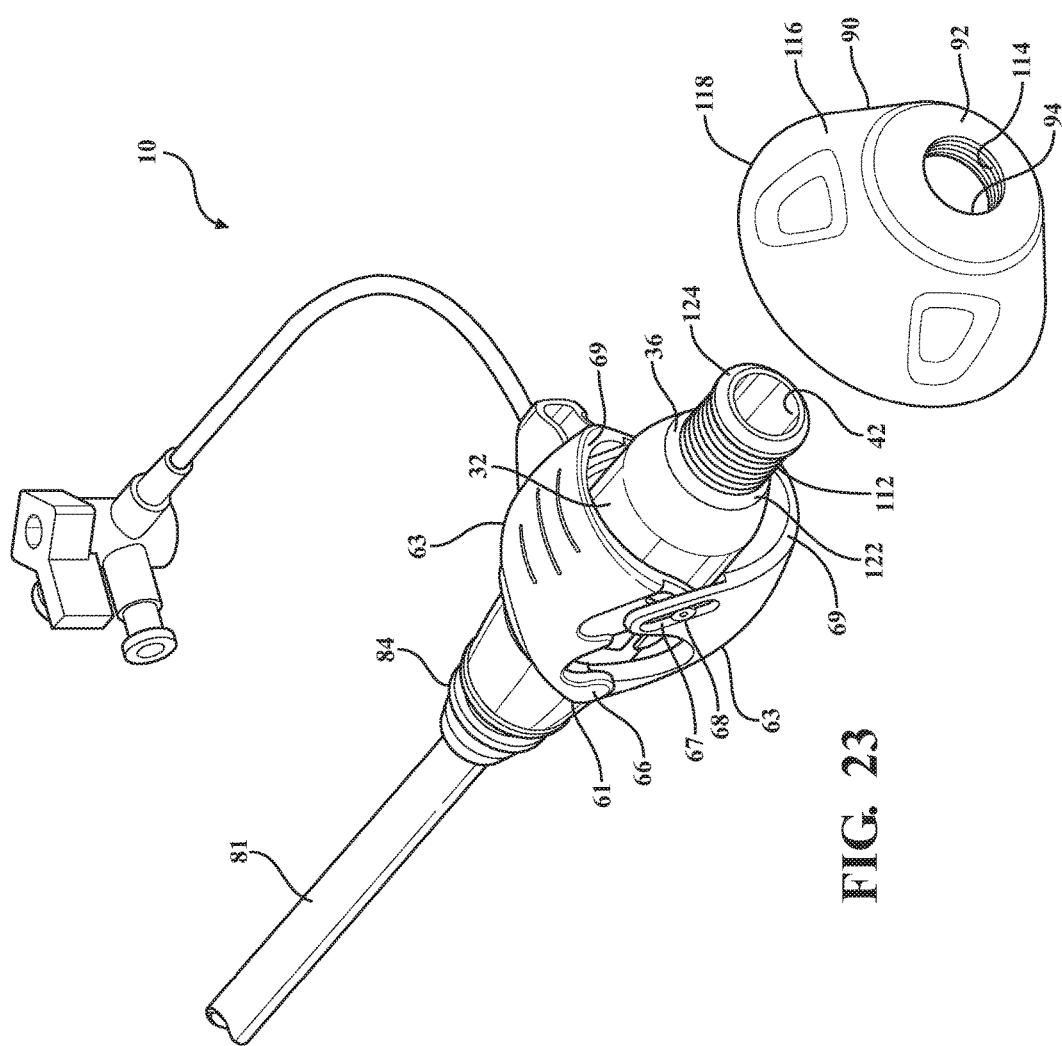
FIG. 23 is an exploded perspective view of the medical valve illustrating a third arrangement of the locking ring in accordance with the principles of the present disclosure.
Figure 24:
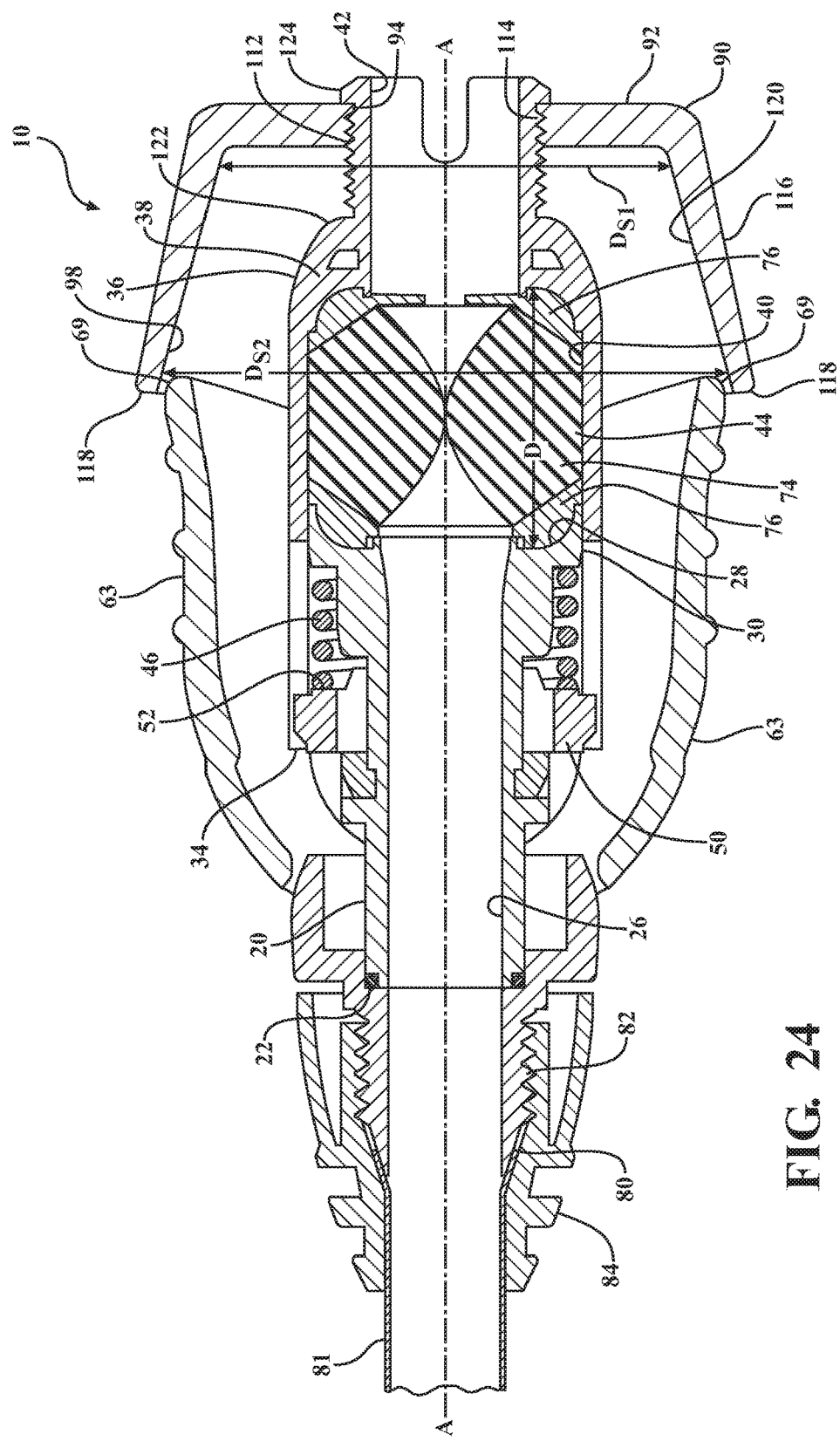
FIG. 24 is a cross-sectional view of the medical valve illustrating the third arrangement of the locking ring disposed in an open position.
Figure 25:
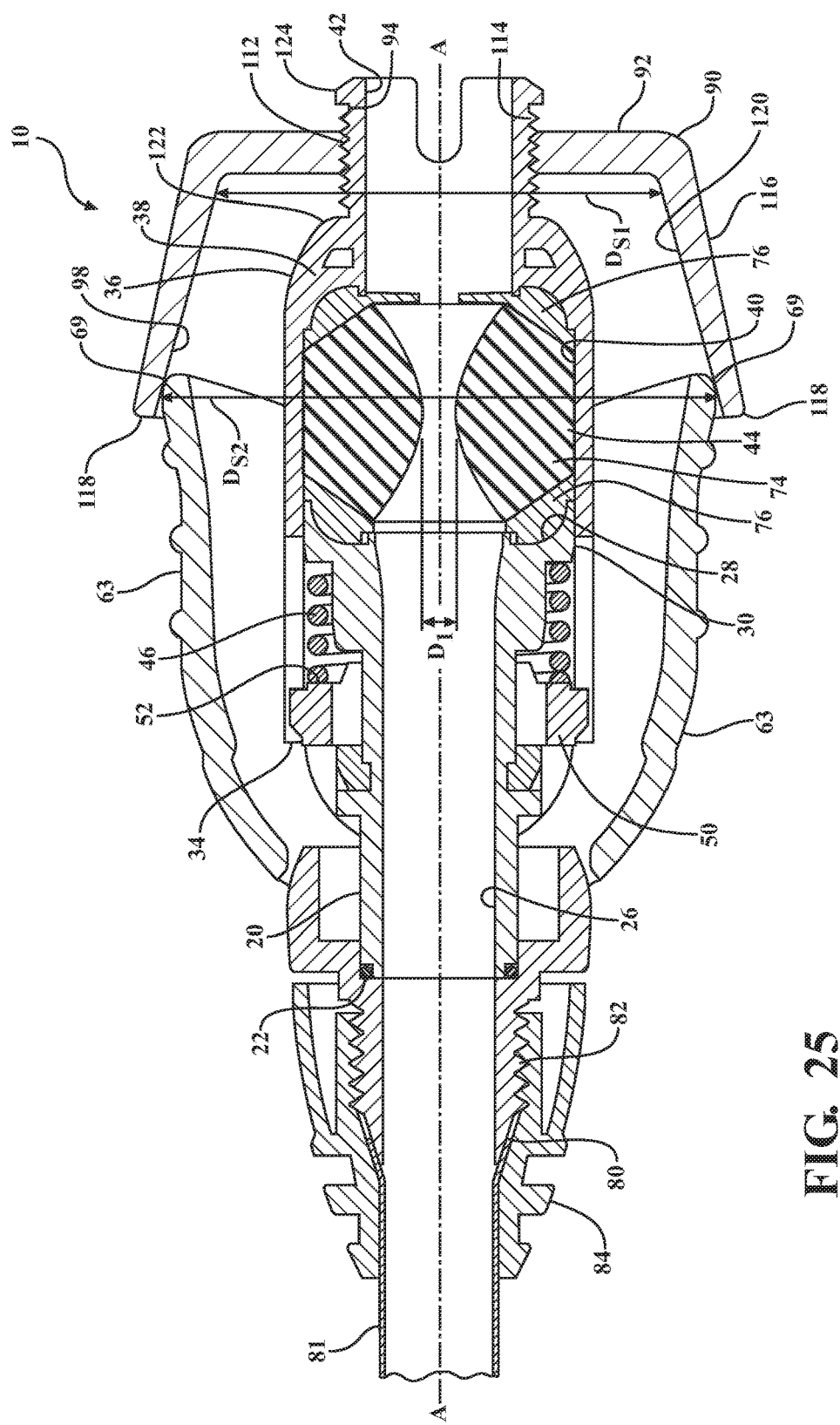
FIG. 25 is a cross-sectional view of the medical valve illustrating the third arrangement of the locking ring disposed in a first intermediate position.
Figure 26:
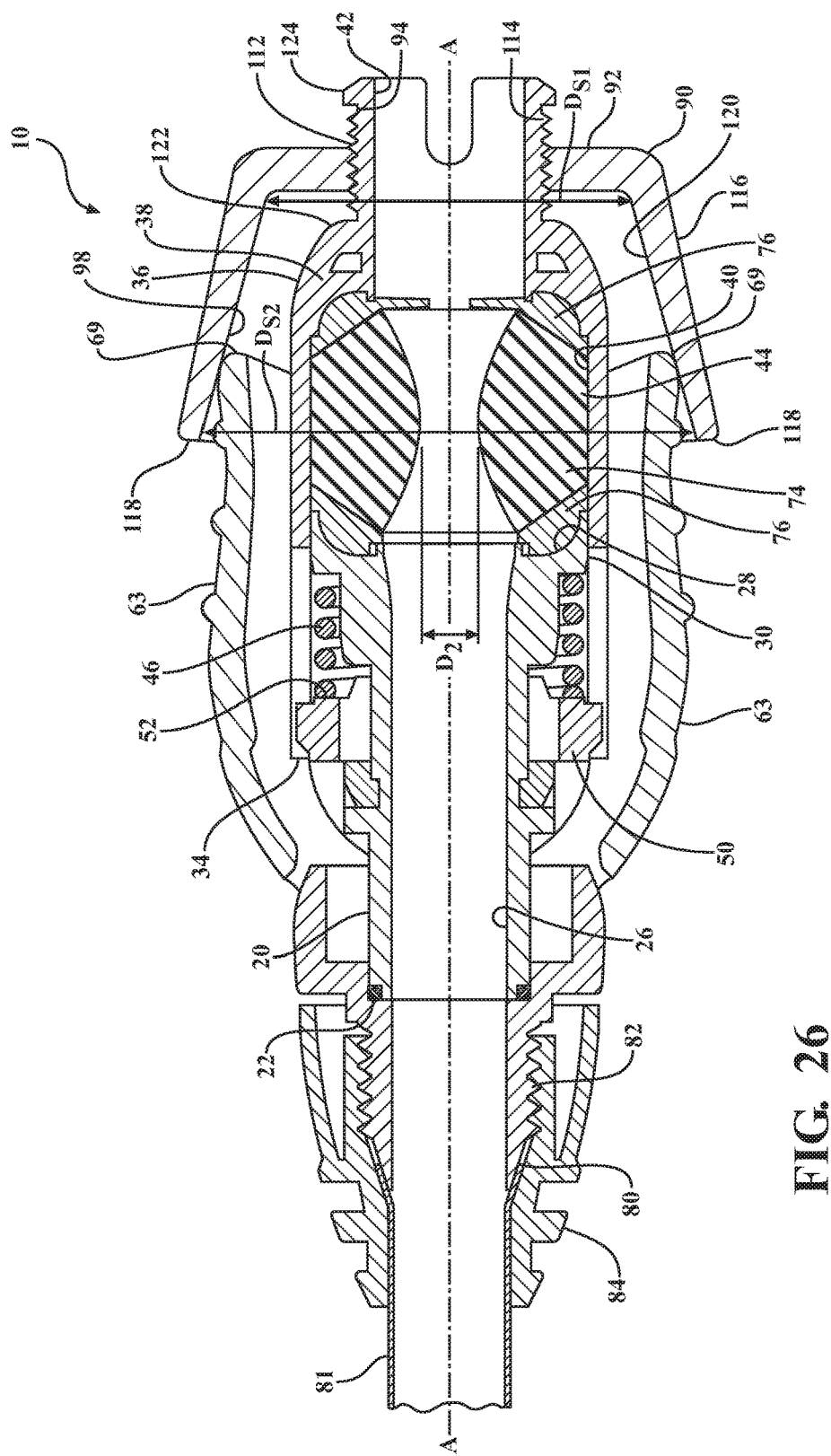
FIG. 26 is a cross-sectional view of the medical valve illustrating the third arrangement of the locking ring disposed in a second intermediate position.

As further illustrated in FIGS. 17-27, in an additional arrangement, the locking ring 90 is also rotatable to at least one intermediate position disposed between the open and closed positions to partially radially compress the pair of lever arms 63 and establish at least one intermediate inner diameter of the elastomeric seal 44 that is greater than the closed inner diameter of the elastomeric seal 44 (which as illustrated in FIGS. 12 and 24 is preferably zero since the elastomeric seal 44 is compressed upon itself) but less than the open inner diameter $D_0$ of the elastomeric seal 44 illustrated in FIGS. 14, 22A, 22B, and 27. As previously discussed, the medical valve assembly 10 must be able to provide a hemostatic seal under a variety of conditions, i.e., accommodate a variety of different sized medical devices 12. Thus, the locking ring 90 including at least one intermediate position advantageously allows a user to quickly and incrementally adjust an inner diameter of the elastomeric seal 44 to accommodate use of differently sized medical devices. In other words, each intermediate position as well as the open position would corresponding to a desired amount of opening of the elastomeric seal 44 of the medical valve 10. For example, a medical device 12 with a larger sized diameter could be utilized when the locking ring 90 is disposed in the open condition while a different medical device with a relatively smaller sized diameter could be utilized when the locking ring 90 is disposed in the at least one intermediate position. The locking ring 90 which incorporates at least one intermediate position also allows the user to place and maintain the elastomeric seal 44 in each of the open and the at least one intermediate positions without the need for the user to continually and constantly maintain a manual radial compression on the pair of lever arms to maintain the appropriate size for allowing insertion of the differently sized devices. Thus, the at least one intermediate position of the locking ring 90 further improves on the user experience during use of the medical valve assembly 10.

As shown in FIGS. 17-18B and 25, in a preferred arrangement the at least one intermediate position includes a first intermediate position disposed between the open and closed positions to incrementally radially compress the pair of lever arms 63 relative to the immediately preceding closed condition and establish a first intermediate inner diameter $D_1$ being greater than the closed (i.e., fully compressed) inner diameter of the elastomeric seal 44. As best shown in FIGS. 19-20B and 25, in a preferred arrangement the at least one intermediate position also includes a second intermediate position disposed between the first intermediate position (FIGS. 17-18B and 25) and the second, open position (FIGS. 14, 22A, 22B, and 27) to incrementally radially compress the pair of lever arms 63 relative to the first intermediate position and establish a second intermediate inner diameter $D_2$ that is greater than the first intermediate inner diameter $D_1$ but less than the open inner diameter $D_0$. The locking ring 90 which incorporates more than one intermediate position allows the locking ring 90 to establish and maintain at least three incrementally sized inner diameters $D_1$, $D_2$, $D_0$ of the elastomeric seal 44 for advantageously accommodating a large variety of differently sized medical devices 12. While three different positions are illustrated and described (two intermediate positions plus one open position), it should be appreciated that additional or less intermediate positions can be utilized without departing from the scope of the subject disclosure, namely because the user requires fewer or more positions to accommodate their differently sized medical devices.

As further illustrated in FIGS. 11-27, the locking ring 90 includes a base 92 rotatably connected to the second valve housing end 36 and defining a base orifice 94 axially aligned with the opening 42 defined by the housing flange 38. The locking ring 90 includes a locking element 96 extending from the base 92 and defining a locking surface 98 disposed in engaged and sliding relationship with the arcuate second lever arm end 36 during rotation of the locking ring 90 between the first and second positions. In other words, the locking surface 98 is configured to slide along the arcuate shape of the second lever arm ends 36 and effectuate a radial compression of the pair of lever arms 63 during rotation.

As best illustrated in FIGS. 11-22B, in a first arrangement of the locking ring 90, the locking element 96 includes a pair of wings 100 disposed in diametrically opposed relationship to one another and each extending from the base 92 to a wing end 102. In this arrangement, a pair of locking flanges 104 each extend axially towards the first valve housing end 34 from a respective one of the wing ends 102 to define the locking surface 98 disposed on each of the wings 100. Each of the locking surfaces 98 concurrently interact with and slide along a respective one of the pair of lever arms 63 during rotation of the locking ring 90 to establish any of the previously mentioned positions.

As best illustrated in FIG. 16, 18B, 20B, and 22B, each of the locking surfaces 98 in the first arrangement of the locking element 96 can present a plurality of steps 106, 108, 110 to incrementally and consecutively radially compress the pair of lever arms 63 and establish and maintain the intermediate positions during rotation of the locking ring 90 between the closed and open positions. For example, as best illustrated in FIGS. 16-18B, the plurality of steps 106, 108, 110 can include a first step 106 to initially engage a respective one of the second lever arm ends 69 of the pair of lever arms 63 and establish the first intermediate position during initial rotation of the locking ring 90 from the first, closed position. As previously discussed, the first intermediate position effectuates a first incremental increase of the distance between the plunger plate 28 and the housing flange 38 and maintains a first intermediate inner diameter $D_1$ of the elastomeric seal 44 which is greater than the closed inner diameter (i.e. compressed and preferably zero) but less than the open inner diameter $D_0$ of said elastomeric seal 44. As further illustrated in FIGS. 16 and 19-20B, the plurality of steps 106, 108, 110 can also include a second step 108 to sequentially engage the respective one of the second lever arm ends 69 of the pair of lever arms 63 and establish the second intermediate position during sequential rotation of the locking ring 90 from the first intermediate position. As previously discussed, the second intermediate position effectuates a second incremental increase of the distance between the plunger plate 28 and the housing flange 38 and maintains a second intermediate inner diameter $D_2$ of the elastomeric seal 44 being greater than the first intermediate inner diameter $D_1$ but less than the open inner diameter $D_0$. As best illustrated in FIGS. 16 and 21-22B, the plurality of steps 106, 108, 110 can also include a third step 110 to sequentially engage the respective one of the second lever arm ends 69 of the pair of lever arms 63 for effectuating a third incremental increase of the distance between the plunger plate 28 and the housing flange 38 to finally establish the open position and maintain the open inner diameter $D_0$ of the elastomeric seal 44. As previously mentioned, additional steps could be added to the locking ring 90 to incorporate additional incremental increases of the inner diameter as required by the user.

Figure 27:
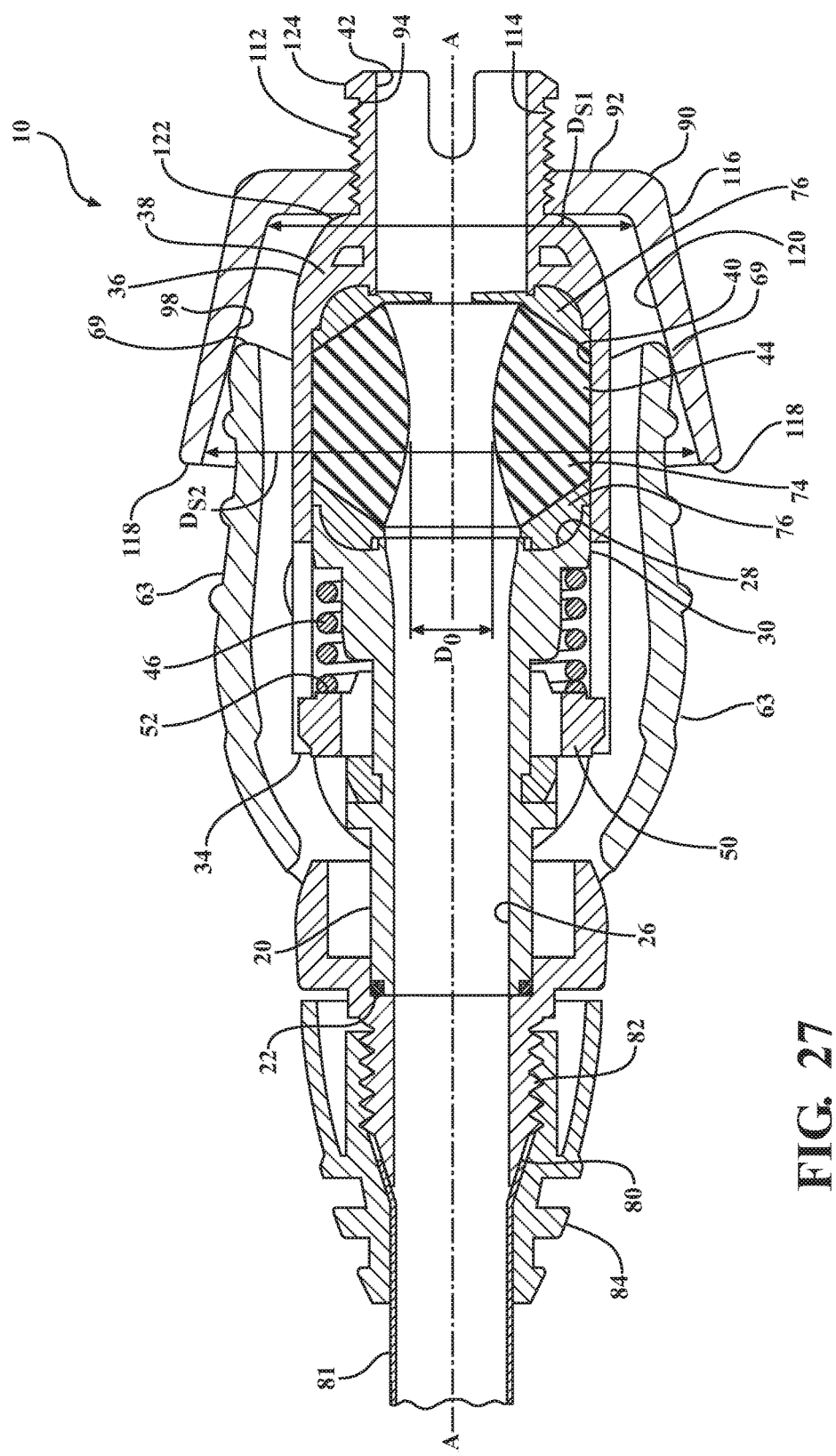
FIG. 27 is a cross-sectional view of the medical valve illustrating the third arrangement of the locking ring disposed in an closed position.

As best illustrated in FIG. 23, in another arrangement of the locking ring 90, the valve housing 32 defines valve threads 112 disposed adjacent the second valve housing end 36. The base 92 of the locking ring 90 correspondingly defines locking threads 114 extending concentrically around the base orifice 94 and threadingly engaged with the valve threads 112 to establish the rotatable connection between the locking ring 90 and the valve housing 32. In this arrangement, the locking element 96 includes a shroud 116 extending concentrically around the axis A and extending between the base 92 and a shroud end 118 to define a shroud inner surface 120 that establishes the locking surface 98. As best illustrated in FIGS. 24-27, the locking ring 90 is rotatable about the valve threads 112 to axially advance the locking ring 90 from the first, closed position (as shown in FIG. 24) wherein the shroud end 118 is disposed in spaced relationship with the second lever arm ends 69 of the pair of lever arms 62 to the second, open position (as shown in FIG. 27) wherein the shroud inner surface 120 effectuates a full and complete radially compression of the pair of lever arms 63. The shroud 120 has a first shroud diameter $D_{S1}$ disposed and extending adjacent the base 92 and a second shroud diameter $D_{S2}$ disposed and extending adjacent the shroud end 118, with the second shroud diameter $D_{S2}$ sized greater than the first shroud diameter $D_{S1}$ to define a ramped or tapered locking surface 98. As shown in FIGS. 24-27, the ramped locking surface 98 incrementally and sequentially radially compresses the pair of lever arms 63 during movement of the locking ring 90 from the first, closed position (FIG. 24) to the second, open position (FIG. 27). In other words, as the locking ring 90 is axially advanced along the valve threads 112, the ramped locking surface 98 initially engages the second lever arm ends 69 and radially compresses the pair of lever arms 63 as the shroud inner diameter narrows from the second shroud diameter $D_{S2}$ towards the first inner shroud diameter $D_{S1}$.

As will be appreciated from the aforementioned disclosure, the ramped locking surface 98 establishes a plurality of intermediate positions as the locking ring 90 is axially advanced along the valve threads 112 that can be tailored by the user anywhere between the first, closed position and the second, open position. In other words, since each of the plurality of intermediate positions are established by rotating the locking ring 90 to different axial positions along the valve threads 112, each different axial location effectuates an incremental and sequential increase of the inner diameter of the elastomeric seal 44, with each intermediate inner diameter of the elastomeric seal 44 being greater than a preceding one of the plurality of axial intermediate positions and less than a subsequent one of said plurality of axial intermediate positions along the valve threads 112. Thus, a user of the medical valve assembly 10 is provided with increased flexibility to establish an exact size of the inner diameter that is specifically sized to the corresponding medical device 12 for insertion through the medical valve assembly 10. Once this preferred inner diameter size is established by the user, the locking ring 90 can be left in its axial position along the valve threads 112 to maintain this desired inner diameter size without requiring the user to manually maintain compression of the pair of lever arms 63. Thus, the shroud of the locking ring 90 further improves on the user experience during use of the medical valve assembly 10.

As best illustrated in FIGS. 24-27, the second valve housing end 36 defines a stop 122 and the valve threads 112 extend from the stop 122 and terminate at a lip 124 defined by the valve housing 32. Thus, as best illustrated in FIG. 24, the base 92 of the locking ring 90 is disposed in abutting relationship with the lip 124 in the first, closed position and, as best illustrated in FIG. 27, is axially advanced into abutting relationship with the stop 122 to establish the second, open position.

In any arrangement of the medical valve assembly 10, the elastomeric seal 44 can include an inner portion 74 and an outer portion 76 disposed axially outwardly from the inner portion 74. In a preferred embodiment, the inner portion 74 is made from a first material having a first durometer value and the outer portion 76 is made from a second material having a second durometer value being greater than the first durometer value. In other words, the elastomeric seal 44 includes an outside portion 76 that is harder than an inside portion 74. As further shown in FIGS. 4A and 4B, the outer portion 76 of the elastomeric seal 44 is disposed in compressed relationship with the plunger plate 28 and the housing flange 38. In a preferred embodiment, the plunger plate 28 and the housing flange 38 can include curved portions 78 to improve the retention and compression of the outer portions 76 of the elastomeric seal 44.

As best shown in FIG. 4, the tube 20 has a tapered portion 80 disposed adjacent the first tube end 22 for fitting a sheath 81 over the tube 20. The tube 20 includes nose cap threads 82 disposed adjacent the first tube end 22 and a nose cap 84 is threadingly secured to the first tube end 22 for establishing a compression fit of the sheath between the nose cap 84 and the tapered portion 80 of the tube 20. Although not expressly shown, a wiper seal can be disposed within the passageway 26 between the elastomeric seal 44 and the first tube end 22 to provide a level of hemostasis around a larger device while the elastomeric seal 44 is opened for insertion of the medical device 12. Alternatively, as best shown in FIGS. 5, 12, 14, 18, 20, 22, and 24-26, a wiper seal 86 can be incorporated into the elastomeric seal 44 and extends radially inward from one of the outside portions 76. As a result, when the elastomeric seal 44 is inserted in the cavity 40, the wiper seal 86 is disposed adjacent the opening 42 of the valve housing 32.

It will be appreciated by those skilled in the art that the medical valve assembly 10' shown in FIGS. 8 and 9 can be equipped with the compression type manual actuator 62 shown in FIGS. 3, 4 and 7 or, in the alternative, the pull-type manual actuator 60 shown in FIG. 6. Likewise, alternative configurations are contemplated for manual actuators that function to controllably vary the relative axial position between two components for proportionately controlling the compression load applied to an elastomeric seal to regulate an internal opening dimension defined thereby.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A medical valve assembly for use in inserting a medical device into a body vessel of a patient, comprising:
   a tube extending between a first tube end and a second tube end to define a passageway extending along a longitudinal axis between said ends;
   a plunger plate extending radially from said second tube end of said tube;
   a valve housing surrounding said tube about said second tube end and extending from a first valve housing end to a second valve housing end;
   said valve housing including a housing flange extending radially inwards from said second valve housing end and disposed in spaced relationship with said plunger plate to define a distance extending therebetween;

an elastomeric seal compressed between said plunger plate and said housing flange and having an inner diameter for establishing a variable seal of the medical valve assembly;

a compression member disposed within said valve housing and biased against said plunger plate for decreasing said inner diameter to establish a closed inner diameter of the elastomeric seal and a respective closed condition of the medical valve assembly;

a pair of lever arms pivotably connected to said valve housing and radially compressible to overcome the bias of said compression member and effectuate axial movement of said valve housing relative to said tube to increase the distance between said plunger plate and said housing flange and increase said inner diameter of said elastomeric seal form the closed condition; and a locking ring rotatably connected to said second valve housing end and rotatable relative to said pair of lever arms to establish and maintain a radially compressed condition of said pair of lever arms and a respective increased inner diameter of said elastomeric seal.

2. A medical valve assembly as set forth in claim 1, wherein said locking ring is rotatable from a closed position wherein said locking ring is disposed in spaced and non-engaging relationship with said pair of lever arms to establish a closed condition of said elastomeric seal to an open position wherein said locking ring engages and radially compresses said pair of lever arms to establish and maintain an increased inner diameter of said elastomeric seal and a respective open condition of the medical valve assembly.

3. A medical valve assembly as set forth in claim 2, wherein said locking ring is rotatable to at least one intermediate position disposed between said open and closed positions to partially radially compress said pair of lever arms and establish at least one intermediate inner diameter of said elastomeric seal being greater than said closed inner diameter of said elastomeric seal but less than said open inner diameter of said elastomeric seal.

4. A medical valve assembly as set forth in claim 3, wherein said at least one intermediate position includes a first intermediate position disposed between said open and closed positions to incrementally radially compress said pair of lever arms relative to said closed condition and establish a first intermediate inner diameter being greater than said closed inner diameter of said elastomeric seal, and wherein said at least one intermediate position includes a second intermediate position disposed between said first intermediate position and said second position to incrementally radially compress said pair of arms relative to said first intermediate position and establish a second intermediate diameter being greater than said first intermediate inner diameter but less than said open inner diameter.

5. A medical valve assembly as set forth in claim 2, wherein said housing flange defines an opening aligned on said axis and sized to receive the medical device, and wherein said locking ring includes a base rotatably connected to said second valve housing end and defining a base orifice axially aligned with said opening.

6. A medical valve assembly as set forth in claim 5, wherein each of said lever arms extend from a first lever arm end pivotably connected to said tube to a second lever arm end disposed adjacent said second valve housing end and having an arcuate shape relative to said axis, and wherein said locking ring includes a locking element extending from said base and defining a locking surface disposed in engaged and sliding relationship with said arcuate second lever arm end during rotation of said locking ring between said closed and open positions.

7. A medical valve as set forth in claim 6, wherein said locking element includes a pair of wings disposed in diametrically opposed relationship to one another and each extending from said base to a wing end, and a pair of locking flanges each extending axially towards said first valve housing end from a respective one of said wing ends to define said locking surface disposed on each of said wings for establishing and maintain said increased open inner diameter of said elastomeric seal when said locking ring is disposed in said open position.

8. A medical valve as set forth in claim 7, wherein each of said locking surfaces presents a plurality of steps to incrementally and sequentially radially compress said pair of lever arms and establish and maintain at least one intermediate position during rotation of said locking arm from said closed to said open position for maintaining at least one intermediate inner diameter of said elastomeric seal being greater than said closed inner diameter of said elastomeric seal but less than said open inner diameter of said elastomeric seal.

9. A medical valve as set forth in claim 8, further comprising:

wherein said plurality of steps includes a first step to initially engage a respective one of said second lever arm ends of said pair of lever arms and establish a first intermediate position during initial rotation of said locking ring from said closed position, wherein said first intermediate position effectuates and maintains a first intermediate inner diameter of said elastomeric seal being greater than said closed inner diameter of said elastomeric seal but less than said open inner diameter of said elastomeric seal;

wherein said plurality of steps includes a second step to sequentially engage said respective one of said second lever arm ends of said pair of lever arms and establish a second intermediate position during sequential rotation of said locking ring from said first intermediate position, wherein said second intermediate position effectuates and maintains a second intermediate inner diameter of said elastomeric seal being greater than said first intermediate inner diameter but less than said open inner diameter of said elastomeric seal; and wherein said plurality of steps includes a third step to sequentially engage said respective one of said second lever arm ends of said pair of lever arms for effectuating a third incremental increase of the distance between said plunger plate and said housing flange to establish said open position and maintain said open inner diameter of said elastomeric seal.

10. A medical valve as set forth in claim 5, further comprising:

said valve housing defining valve threads disposed adjacent said second valve end; and said base of said locking ring defining locking threads extending concentrically around said base orifice and threadingly engaged with said valve threads to establish said rotatable connection between said locking ring and said valve housing.

11. A medical valve as set forth in claim 10, wherein said locking element includes a shroud extending concentrically around said valve axis and extending from said base to a shroud end to define a shroud inner surface for establishing said locking surface, and wherein said locking ring is rotatable about said valve threads to axially advance said locking ring from said closed position wherein said shroud end is disposed in spaced relationship with said second lever arm ends of said pair of lever arms to said open position wherein said shroud inner surface radially compresses said pair of lever arms.

12. A medical valve as set forth in claim 11, wherein said shroud having a first shroud diameter adjacent said base and a second shroud diameter adjacent said shroud end, said second shroud diameter being greater than said first shroud diameter to define a ramped locking surface for incrementally and sequentially radially compressing said pair of lever arms during movement of said locking ring from said closed position to said open position.

13. A medical valve as set forth in claim 12, wherein said ramped locking surface establishes a plurality of intermediate positions during axial movement of said locking ring from said closed position to said open position, and wherein each of said plurality of intermediate positions effectuate an incremental and sequential increase of said distance between said plunger plate and said housing flange and maintains a respective intermediate inner diameter of said elastomeric seal being greater than a preceding one of said plurality of intermediate positions and less than a subsequent one of said plurality of intermediate positions.

14. A medical valve as set forth in claim 13, wherein said second valve housing end defines a stop and said threads extend from said stop and terminate at a lip, and wherein said base of said locking ring is disposed in abutting relationship with said lip in said closed position and is axially advanced into abutting relationship with said stop to establish said open position.

* * * * *